(12) United States Patent
Bernié et al.

(10) Patent No.: US 6,301,373 B1
(45) Date of Patent: Oct. 9, 2001

(54) PAPER QUALITY DETERMINATION AND CONTROL USING SCALE OF FORMATION DATA

(75) Inventors: Jean-Philippe Bernié, Montreal; W.J. Murray Douglas, Baie d'Urf″, both of (CA)

(73) Assignee: McGill University, Quebec (CA)

(*) Notice: Subject to any disclaimer, the term of this patent is extended or adjusted under 35 U.S.C. 154(b) by 0 days.

(21) Appl. No.: 09/164,562

(22) Filed: Oct. 1, 1998

(51) Int. Cl.⁷ .................................................... G06K 9/00

(52) U.S. Cl. .......................................... 382/108; 382/112

(58) Field of Search ..................... 382/100, 112, 382/181, 224, 250, 276, 280, 282, 286; 356/238.1, 429; 73/159; 702/57, 66, 67, 68, 71, 81, 82, 83, 84

(56) References Cited

U.S. PATENT DOCUMENTS

| | | | |
|---|---|---|---|
| 4,213,708 | * | 7/1980 | Lucas ................................. 356/429 |
| 4,513,441 | * | 4/1985 | Henshaw ............................. 382/280 |
| 4,857,747 | * | 8/1989 | Bolton et al. ..................... 250/559.24 |
| 4,922,337 | * | 5/1990 | Hunt et al. .............................. 348/88 |
| 4,931,657 | * | 6/1990 | Houston et al. .................. 250/559.08 |
| 5,047,652 | * | 9/1991 | Lisnyansky et al. ............ 250/559.01 |
| 5,563,809 | * | 10/1996 | Williams et al. ...................... 702/84 |
| 5,684,707 | * | 11/1997 | Rogowski ............................. 700/129 |
| 5,748,780 | * | 5/1998 | Stolfo ................................. 382/232 |
| 5,865,120 | * | 2/1999 | Gross ................................. 101/483 |
| 5,974,160 | * | 10/1999 | Shiratori et al. .................... 382/112 |
| 6,035,072 | * | 3/2000 | Read ................................. 382/275 |

OTHER PUBLICATIONS

Effect of Papermaking Variables on Formation, by John F. Waterhouse, pp.: 129–134, vol. 76, No. 9, Tappi Journal.

Comparison of Four Paper Imaging Techniques:B–Radiography, Electrography, Light Transmission, and Soft X–Radiograpby, by Hiroshi Tomimasu et al.; pp.: 165–176, Jul. 1991, Tappi Journal.

"Specific Perimeter—A Graininess Parameter for Formation and Print–Mottle Tectures", by B.D. Jordan et al., pp.: 476–482, Paperi ja Puu—Pâpperoch Trä 6–71986./.

"Level Crossing Statistics: A Simple Image Analysis Approach to Formation and Print Quality Assessment", by R.J. Trépanier et al, pp.: 147–152, 1996 Process & Product Quality Conference.

"The Measurement of Formation", by Otto J. Kalilmess, p.: 117, Tappi Journal, vol. 67, No. 11.

"Dynamics of Sheet Formation on the Fourdrinier Machine", by P. E. Wrist, pp.: 839–899, Research Laboratories, The Mead Corporation, Chillocothe, Ohio, U.S.A.

(List continued on next page.)

Primary Examiner—Andrew W. Johns
Assistant Examiner—Shervin Nakhjavan
(74) Attorney, Agent, or Firm—Michael D. Bednarek; Shaw Pittman LLP

(57) ABSTRACT

A quality of a sheet material, such as unprinted paper, is determined by acquiring an image of the surface of the sheet material and analyzing the image to determine the intensity of local nonuniformity as a function of scale of formation. A meaningful interpretation of the sheet material quality is possible using the scale of formation. Correlations between sheet material qualities, such as cloudiness, cross-directional strength, etc., and the scale of formation allow for rapidly acquired images to provide useful indicators of sheet material quality. Normalizing the sheet material formation line with respect to a desired standard sheet allows for a useful graphical display of the sheet material quality.

27 Claims, 21 Drawing Sheets

OTHER PUBLICATIONS

"A Formation Tester Which Graphically Records Paper Structure", by G. Burkhard, et al, pp.: T–319–T–334, Pulp and Paper Magazine of Canada, Jun. 1960.

"The Role of Fundamental Research in Paper Making", by James Brander, PhD., pp.: 767–777, Publishes by Mechanical Engineering Publications Limited, London.

"The Characterization of Paper Formation", Part 2, Thierry Cresson et al., pp.: 175–185, Dec. 1990, Tappi Journal.

"The Characterization of Paper Formation", Part 3, by Thierry Cresson et al., pp.: 167–175, Feb. 1991, Tappi Journal.

"Description of the Spatial Gray Level Dependence Method Algorithm", by Thierry Cresson et al., pp.: 220–222, Dec. 1990, Tappi Journal.

"Formation Measurement—How It Relates to Process and Final Quality", by Ray Shead, pp.: 24–28, Paper Technology, Sep. 1993 Formation.

"A Comprehensive Method for the Description of Mass Distribution in Sheets and Flocculation and Turbulence in Suspensions", by Bo Norman et al., pp.: 807–818, Nov. 15, 1972, Svensk Papperstidning arg. 75.

"Mass Distribution and Sheet Properties of Paper", by B. Norman et al., pp.: 7–73, Swedish Forest Products Research Laboratory, Stockholm.

"How Formation Should be Measured and Characterized", by Isko M. Kajanto et al., The Finnish Pulp and.: Paper Research Institute, Helsinki.

"Analysis of Optical Surface Properties of Printed and Unprinted Papers With Image ANalyzer, Part 1; Periodic and Stochastic Variations of Gray Scale Values", Code 122–23958, pp.: 1–35, Institu für Papierfabrikation an der TH Darmstadt, Alexanderstrasse 8, D–6100, Darmstadt.

"The Formation Spectrum", by Bo Norman pp.: 104, Jul. 1985, Tappi Journal.

"Enhancing Visibility of Wire–Mark By Image Analysis", by S.J. l'Anson et al,, p.: J22J26, Journal of Pulp and Paper Science, vol. 17, No. 1, Jan. 1991.

"A rational Approach to Formation Analysis ams Spreadsheet Schema for Data Interpretation", by C.T.J. Dobson, pp.: 153–16, May 1993, Tappi Journal.

"Modeling Flocculation, Part 1, Random Disk Model"., by R.R. Farnwood et al., pp.:J348–J356, Journal of Pulp and PaperScience, vol. 21, No .10, Oct. 1995.

"Interpreation of Formation of Paper", by C.T.J. Dobson et al., pp.: 1–13, APPITA Annual Conference, Rotorua NZ, Apr. 19–23, 1993.

Flocculation, Dispersion and Dynamic Scenarios for Formation, by C.T.J. Dobson et al., pp.: 264–272, Nordic Pulp andPaper Research Journal, No. 2, 1993.

"Overview of Texture Analysis of Print and Paper", by N.G. Nguyen et al., pp.: 933–942, Paperi ja Puu—Paper and Timber Aug. 1989.

"Light Scanning System Provides Qualitative Formation Measurement", by Otto J. Kallmes et al., pp.: 99–105, Pulp and Paper Apr. 1987.

"User–Friendly System Analyzes Paper Formation, Dirt Spect Content, and Solid–print nonuniformity ", by Roland J. Trépanier, Dec. 1989 Tappi Journal.

"The Dagbladet full–scale printing trials", Part 2: Print–quality evaluation by subjective and image analysis, Elisabeth L. Berli, Klaus Moller, Age Hansen, and Bent Foyn. Newsprint Trials, Nov. 27, 1995, vol. 77, No. 4 Tappi Journal, pp 151–159.

* cited by examiner

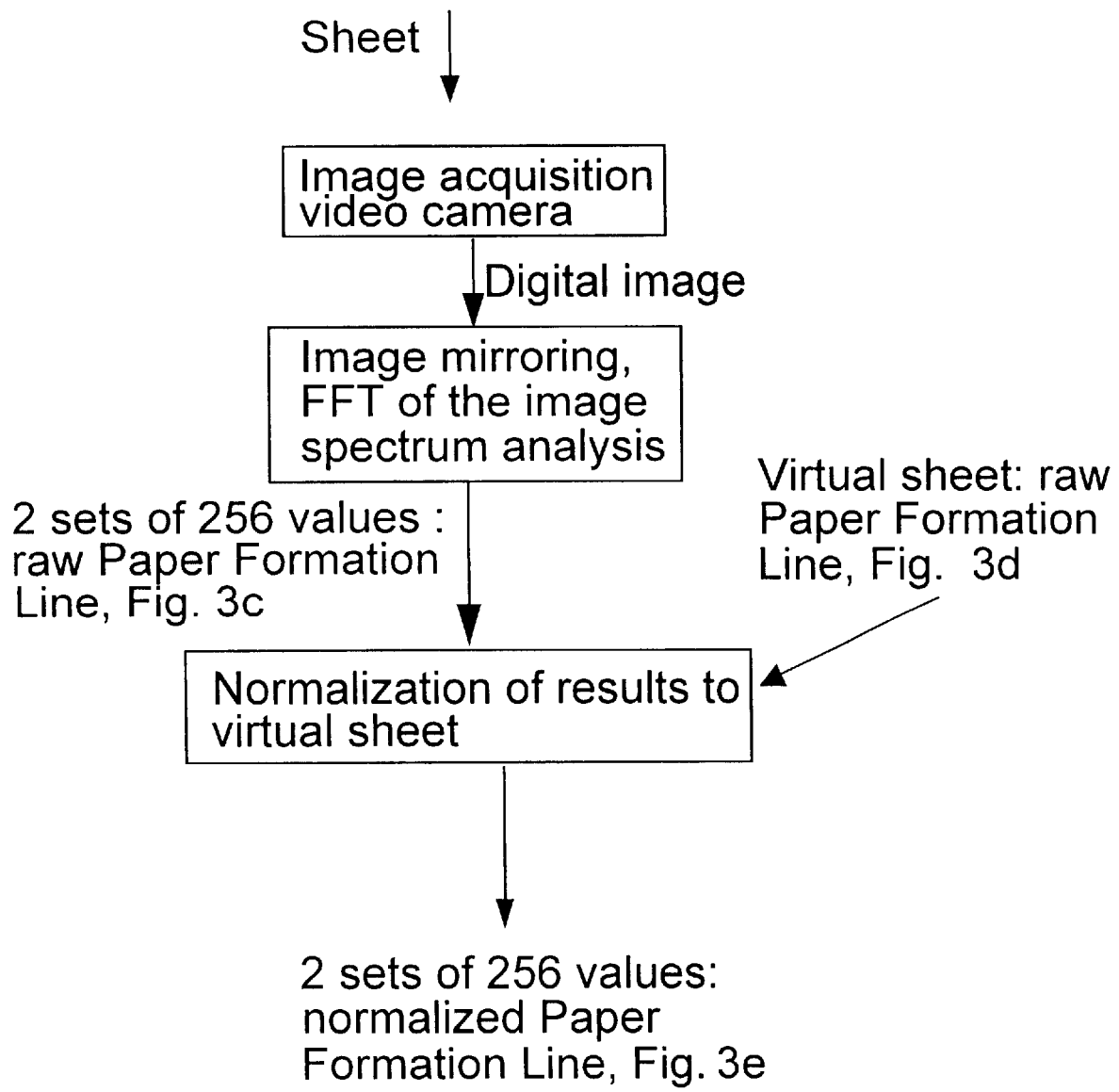

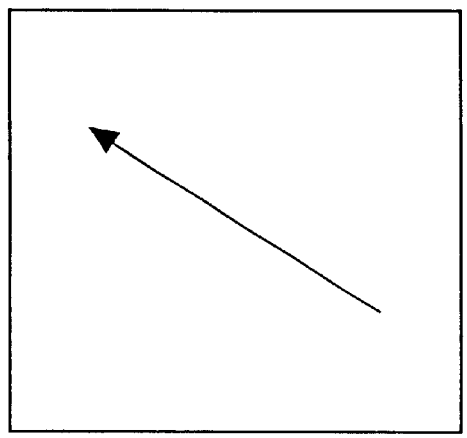
Original image
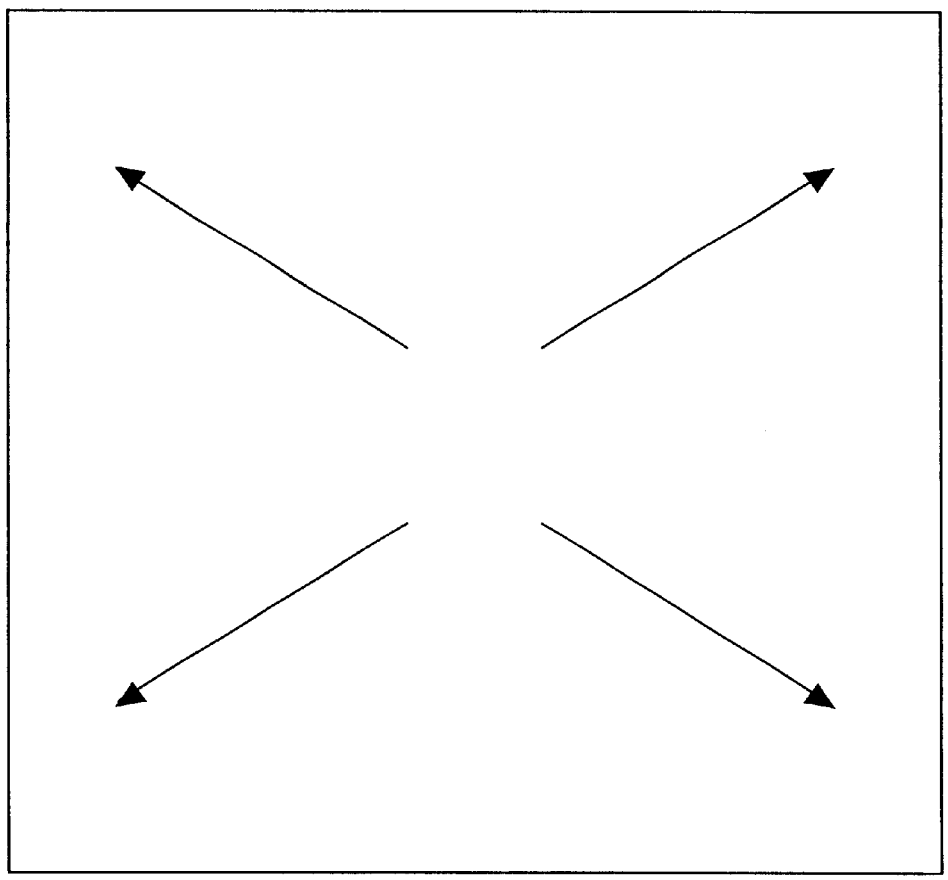
Mirrored image
FIG. 3b

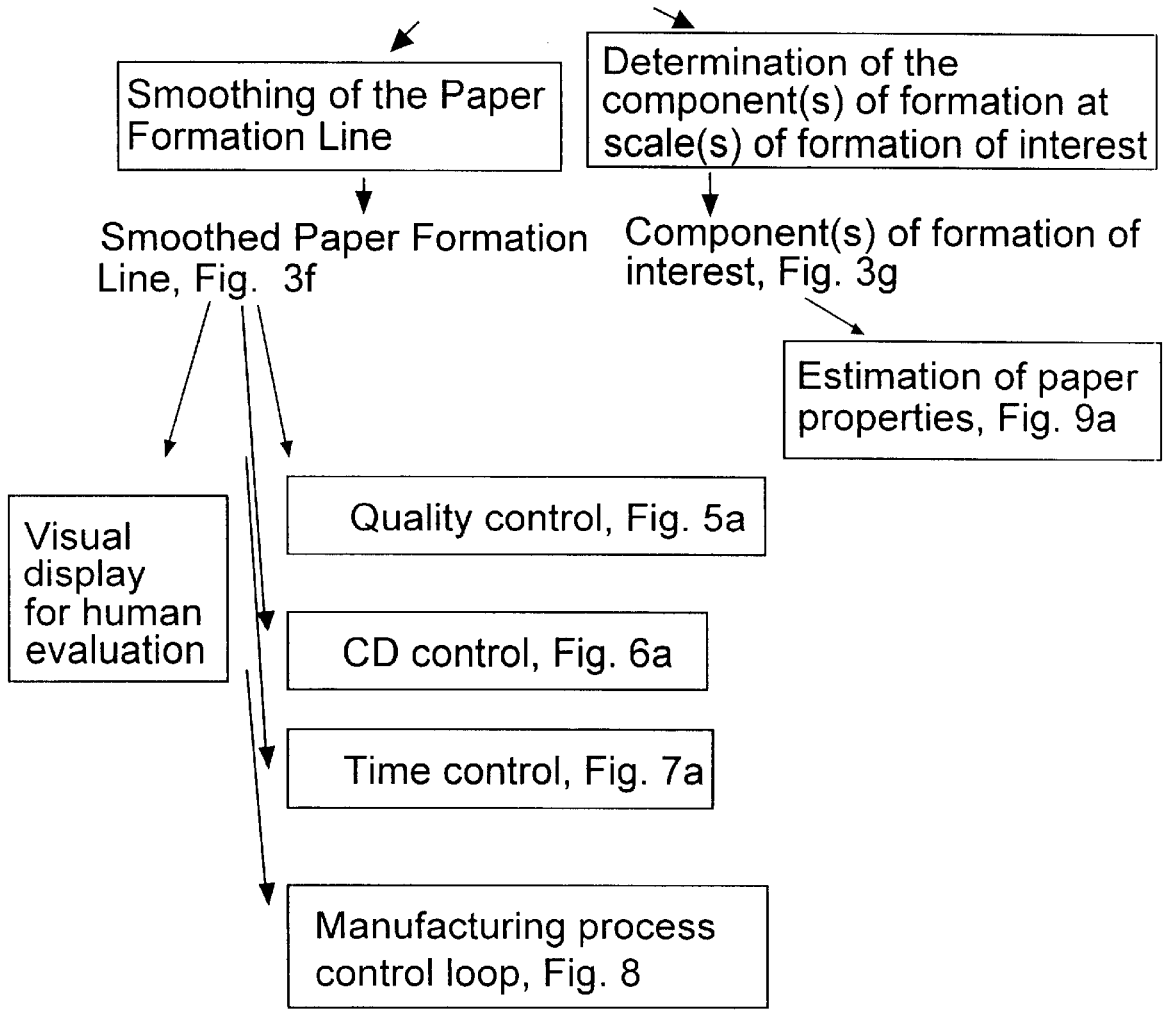
$\overline{\pm\pm\square}\negthinspace\square\negthinspace\square 4$

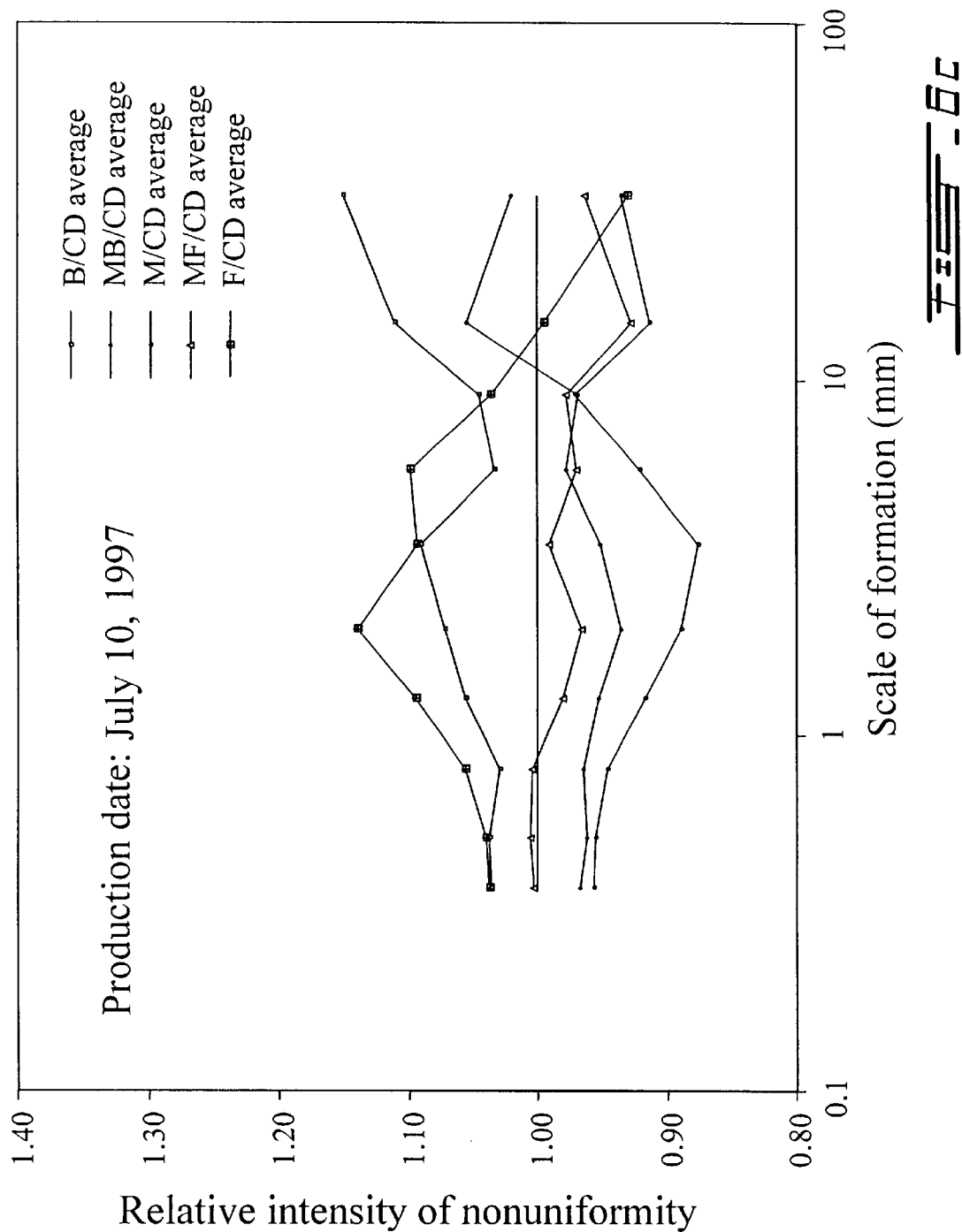

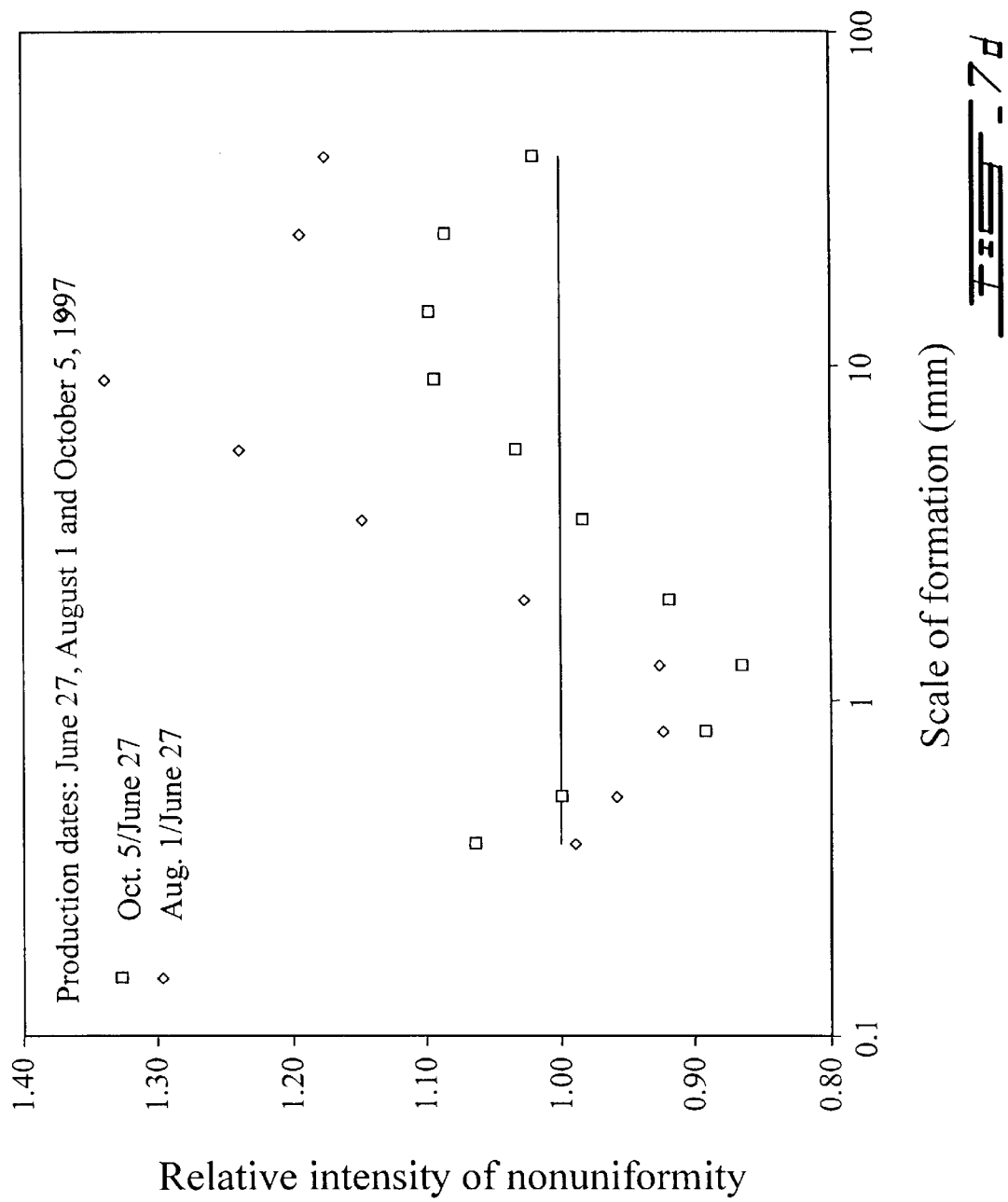

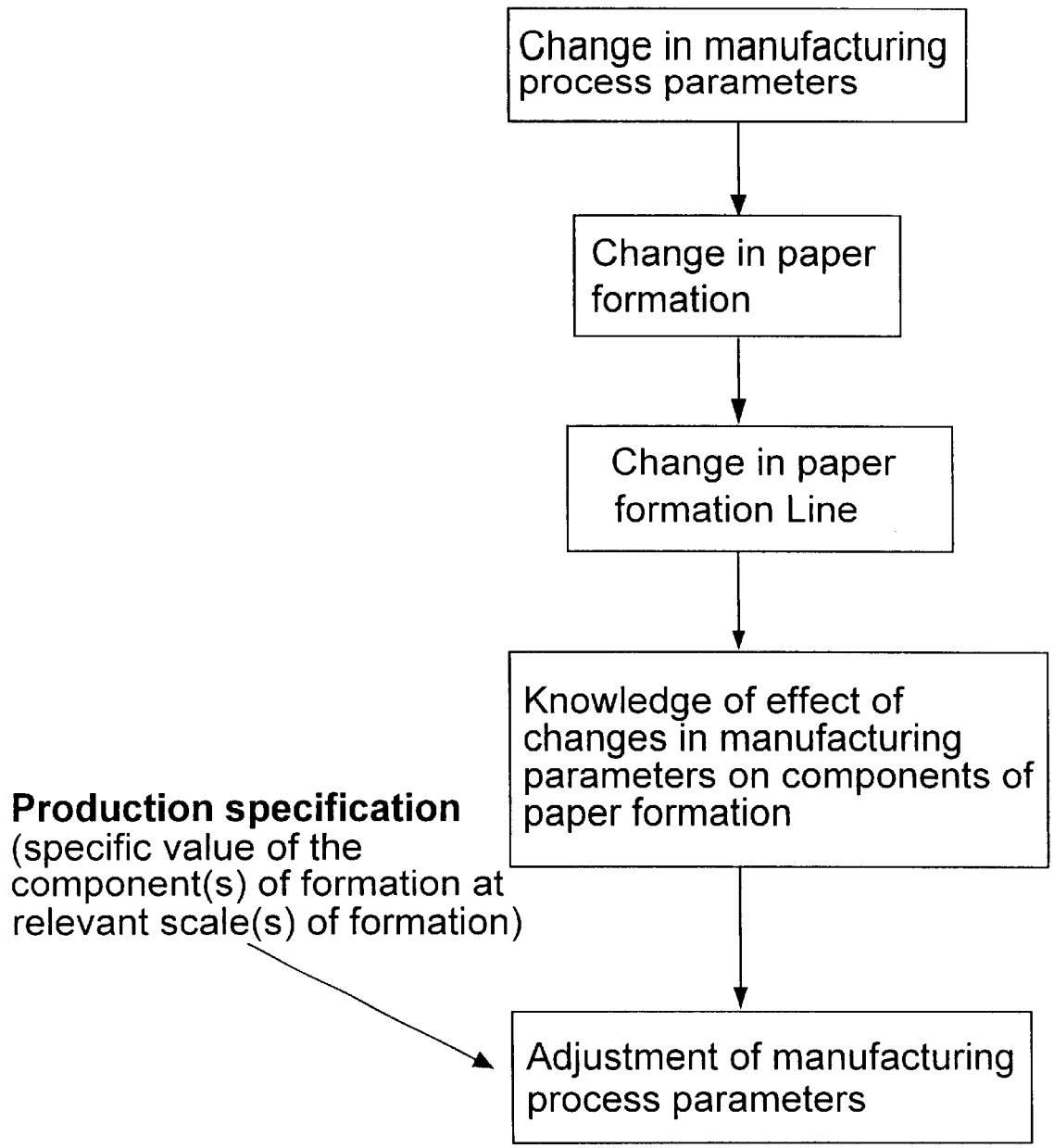

Range of controlling scale of formation:
4-8mm $R^2$ value for this range: 0.56

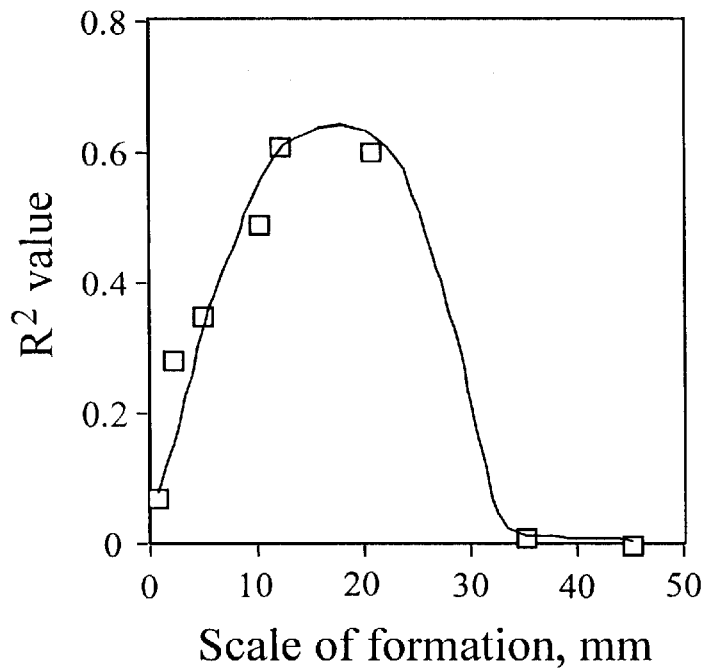
Range of controlling scale of formation: 10-25mm
$R^2$ value for this range: 0.63
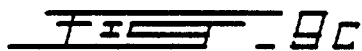
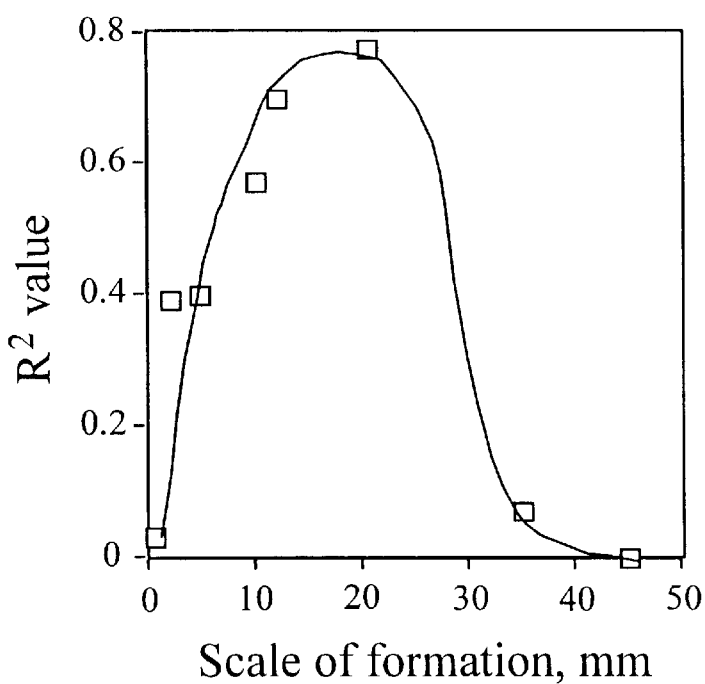
Range of controlling scale of formation: 10-25mm
$R^2$ value for this range: 0.78

PAPER QUALITY DETERMINATION AND CONTROL USING SCALE OF FORMATION DATA

FIELD OF THE INVENTION

The present invention relates to an improved method of determining paper quality and evaluating the performance of the process of manufacturing of paper, and to the use of paper quality information for the purposes of controlling paper machines and other aspects of the papermaking process, with the objective of optimizing paper quality. The invention further relates to an improved method of determining print quality through characterizing the nature of print nonuniformity. The present invention also relates to materials other than paper which are produced as sheets, films, webs, laminates, textiles, fabrics which have qualities or characteristics defined by surface image nonuniformity characteristics, and to the control of the processes used in manufacturing such materials.

BACKGROUND OF THE INVENTION

Paper is a complex, porous, fibrous material, produced by high technology manufacturing processes. These processes include the pulping operation which creates the pulp from the basic raw or recycled fibrous material, addition of components other than the pulp, then the production of paper on the papermachine. Because of the nature of paper and of the process by which it is produced, paper without local nonuniformity in its structure does not exist. This local nonuniformity of the structure of the sheet is the uneven distribution of fibers across the sheet, and is referred to as its formation.

Papermakers try to minimize the extent of this nonuniformity in order to have a good formation. As papermachines produce sheets up to about 10 meters wide in a high speed process, papermakers are concerned not only by the quality of the paper they produce, but by the consistency of this quality across the width of the machine as well as over time. In practice the quality of paper varies with time and with position across the width of the roll. Papermakers try to minimize such variability in order to achieve the objective of a constant, high quality product. They attempt to control the variables of the pulping process, any addition of chemicals to the furnish provided to the papermachine, as well as the design, operation and control of the papermachine in order to produce paper, over time and across the width of the papermachine, having minimum local nonuniformity in sheet structure, that is, of best possible formation. Quality of paper formation is the immediate and direct consequence of the furnish provided to the papermachine, and of the design, operation and control of the papermachine that produces the sheet.

The quality of formation, so determined by the many variables in papermaking, in turn affects the properties of the sheet which characterize paper quality and thereby influence its market value; optimizing paper formation is therefore central to the objective of producing high quality paper. These paper properties include strength properties, mechanical properties, printability and coatability. While it would be desirable to control the papermaking process according to direct measurement of these properties, the extent to which this procedure is possible is very limited for some properties, and impossible for other properties, because of the long measurement time required and of the complex relationship between these numerous properties and the papermaking parameters. As formation has a strong influence on paper properties, a simpler strategy available to papermakers would be to measure the quality of formation, then to control the process parameters in order to optimize the formation quality, thereby optimizing paper quality and value. Implementation of this strategy of optimizing paper quality by optimizing paper formation is limited because current commercial test instruments for formation measurement provide results which correlate poorly with paper properties. These low correlations may be the result of the current measurements not reflecting faithfully the essential characteristics of sheet formation. As paper formation is the local nonuniformity of sheet structure, measurement of the extent and nature of the nonuniformity of paper structure is now considered.

Determination of the two-dimensional map of the local value of mass per unit area of the sheet, grams/square meter, $g/m^2$, referred to as the local grammage of the sheet, provides the basic information about sheet structure. Radiographic techniques provide such a map of local grammage but are slow and suffer from the practical disadvantages of radiographic procedures. Therefore it has long been common practice to use the alternative of light transmission technique to generate maps of local opacity of paper, a satisfactory approximation of local grammage maps. The key advantage for the use of image analysis is that with a good equipment a map of local opacity of the sheet can be determined in less than a second, very much faster than any radiographic technique. Determination of the strength and mechanical properties of paper and the quality of printing or coating on the paper may take from minutes to months, depending on the property. The potential for use of quality of formation thus determined for fast control of papermaking is therefore evident.

The next step is how to process the information contained in such maps of local nonuniformity of paper, whether determined as local grammage or local opacity. A widely practiced method is to use all the values of the local measurement contained in such a map to compute simply the coefficient of variation of the distribution of these local measurements, i.e. the standard deviation of the local measurement divided by the sheet average value of these measurements. If the measurements are of local grammage, this coefficient of variation is defined as formation number. If the measurement is of local grey level, this index is often referred to as a grey-level based formation number.

The advantage of this method of processing the information contained in the map of local nonuniformity is its simplicity, in providing a single number proportional to the total amount of local nonuniformity. Thus, the numerous commercial formation test instruments based on light transmission image analysis currently used around the world provide a single numerical value as an index of formation nonuniformity, which may be an opacity based formation number or proportional to it, or some other single number formation index. The associated disadvantage of this method of processing the data from a map of the local nonuniformity measurements is that all the information contained in the location, on the sheet, of each such local measurement is lost. Thus although current formation test instruments may start by obtaining a two-dimensional map of the location of each measurement of local opacity, most of that information is lost whenever any single number index of formation is determined, as is present practice.

Papermakers have long known that the quality of formation of paper has a big impact on paper properties and have tried correlating these properties with values of the single number index of formation provided by the commercial paper formation measurement instruments. However, these correlations have been found to be disappointingly very low. This contradiction is due to the inadequate measurements of formation provided by these instruments: a single number is necessarily blind to how the nonuniformity of formation is distributed across the sheet, but paper properties are sensitive to the way this nonuniformity is distributed.

For this reason, even decades after the use of single-index formation test instruments became standard practice in paper companies, papermakers and printers still inspect paper visually to evaluate what their formation instruments cannot tell them. With the use of test instruments giving a single number index of formation, the eye has remained the only source of the missing information as to how the local nonuniformity is distributed. Visual inspection is expressed with terms coined by papermakers such as grainy, cloudy, mottled, which evoke some of the limitless patterns for the distribution of nonuniformity across the sheet. This visual inspection is the only way papermakers currently have to evaluate the distribution across the sheet of the local nonuniformity of sheet structure, but this method provides only subjective, observer-dependant, qualitative and oversimplified information. The incentive to go from this subjective information towards quantitative representation of how the nonuniformity of structure is distributed across the sheet has led to much research concerning paper formation.

FIGS. 1a and 1b show two sheets of paper which have exactly the same coefficient of variation of local opacity, i.e. the same grey-level based formation number. It is evident that in spite of having identical values of this index of formation, the formation of these two sheets is in reality very different. The equality of values of grey-level based formation number establishes that the two sheets have the same total amount of local nonuniformity. What is apparent visually from FIGS. 1a and 1b is that this same total amount of local nonuniformity is distributed across these two sheets in two very different ways. The sheet portrayed in FIG. 1a is referred to as of grainy formation because the local nonuniformity is on a small scale, while the sheet of FIG. 1b is described as cloudy because the local nonuniformity is on a larger scale. This example illustrates the necessity of going beyond formation number to characterize the formation of a sheet of paper. FIG. 2 illustrates the steps implemented according to one prior art method which attempts to solve this problem by using Fourier analysis in order to determine how the local nonuniformity is distributed across the sheet. An image of the sheet is obtained by transmission of light, visible or not, or of a laser beam, or of other kind of radiation, to a sensor which creates the corresponding map. In the paper by Wrist, P. E. "Dynamics of sheet formation on the Fourdrinier machine", Oxford Symposium on the Formation and Structure of Paper, p. 839–888(1962), it was proposed to use have frequential analysis methods, on 1- or 2-dimensional data of local nonuniformity of grammage or grey level. In the early 1970s a FFT-based method was described by Norman and Wahren in their article "A comprehensive method for the description of mass distribution in sheets and flocculation and turbulence in suspensions", Svensk Papperstidning, 20, p. 807–818 (1972). The use of 2-dimensional data is preferable because 1-dimensional analysis loses the pronounced anisotropy of paper, crucially important for paper properties. In these studies the results have been presented variously, including in terms of frequency/amplitude, wavelength/amplitude, floc size/floc intensity, which do not provide clear information usable by papermakers for control of paper quality.

The known prior art does not provide a sufficiently accurate, reliable and useful method to analyze paper image data to obtain paper quality.

SUMMARY OF THE INVENTION

It is therefore an object of the present invention to analyze image data from sheet material, such as paper, to obtain scale of formation information and to process the scale of formation information so as to provide improved material quality information.

It is a further object of the present invention to make use of the improved material quality information to adjust or control production parameter used in making the sheet material. Such control may be off-line or on-line, Another object of the invention is to provide a method of determining quantitatively, for materials such as sheets, paper, webs, laminates, textiles, fabrics, how the local nonuniformity of structure of such materials is distributed across the sheet and similarly, determining the local nonuniformity of the printability of surfaces.

A further object of the invention is to establish the utility of this quantitative measure of the distribution of the local nonuniformity of sheet structure by determining the relation between this measure and properties of the sheet which determine its quality. By coupling this technique to the demonstration of its utility, an overall objective is to enable the rapid optimization of product quality by providing a fast and meaningful measurement of the nonuniformity of sheet structure which can be incorporated into a control loop for the operation of the manufacturing process.

According to the invention, there is provided a method of determining a quality of sheet material comprising steps of:

acquiring an image of a portion of a surface of the sheet material;

analyzing the acquired image to determine an intensity of local nonuniformity in the image as a function of a scale of formation;

selecting a predetermined range of the scale of formation responsible for determining the sheet material quality; and generating an output value indicative of the sheet material quality from the intensity of local nonuniformity within the selected range.

The invention also provides a method of quality control analysis of sheet material compared with respect to a reference sheet comprising steps of:

acquiring a first image of a portion of a surface of the reference sheet;

analyzing the first image to determine an intensity of local nonuniformity in the first image as a function of a scale of formation;

acquiring a second image of a portion of a surface of the sheet material;

analyzing the second image to determine an intensity of local nonuniformity in the second image as a function of a scale of formation;

normalizing the intensity of local nonuniformity in the second image with respect to the intensity of local nonuniformity in the first image to obtain a normalized sheet material formation line output data set.

The invention further provides a method of manufacturing sheet material comprising steps of:

acquiring an image of a portion of a surface of the sheet material at at least one transverse location on the sheet material;

analyzing the acquired image to determine an intensity of local nonuniformity in the image as a function of a scale of formation;

generating an output value indicative of the sheet material quality from the intensity of local nonuniformity and the scale of formation;

comparing the output value to an accepted value; and adjusting a manufacturing process parameter in response to the comparing.

The sheet material is preferably unprinted paper, although the invention may be equally applied to other sheet materials and to assessing the quality of print on printed paper.

BRIEF DESCRIPTION OF THE DRAWINGS

The invention will be better understood by way of the following detailed description of a preferred embodiment with reference to the appended drawings, in which:

FIG. 3a is a flow chart representing the method of analyzing paper surface images according to the preferred embodiment;

FIG. 3b shows an original image and a mirrored image in accordance with the preferred embodiment;

FIG. 4 represents schematically options and steps in applying the normalized paper formation line data to various applications;

FIG. 6b and 6c are plots of relative paper formation lines for linerboard at five CD positions on two separate production dates, respectively;

FIGS. 7b, 7c and 7d are plots of intensity of nonuniformity versus scale of formation illustrating the evolution of formation with time for three different grammages of linerboard;

FIG. 8 is a flow chart representing the method of on-line or off-line paper quality optimization according to the preferred embodiment;

FIGS. 9b, 9c and 9d are plots of $R^2$ correlation values versus scale of formation for the cases of offset print quality of uncoated paper, CD tear strength of newsprint, and MD tear strength of newsprint.

DETAILED DESCRIPTION OF THE PREFERRED EMBODIMENT

Figure 1A:
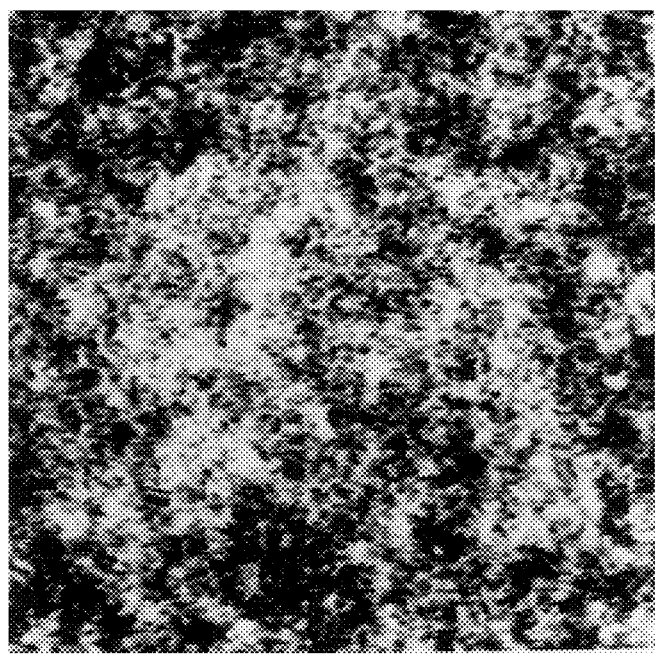
FIGS. 1a and 1b are images of grainy and cloudy paper surfaces respectively.
Figure 1B:
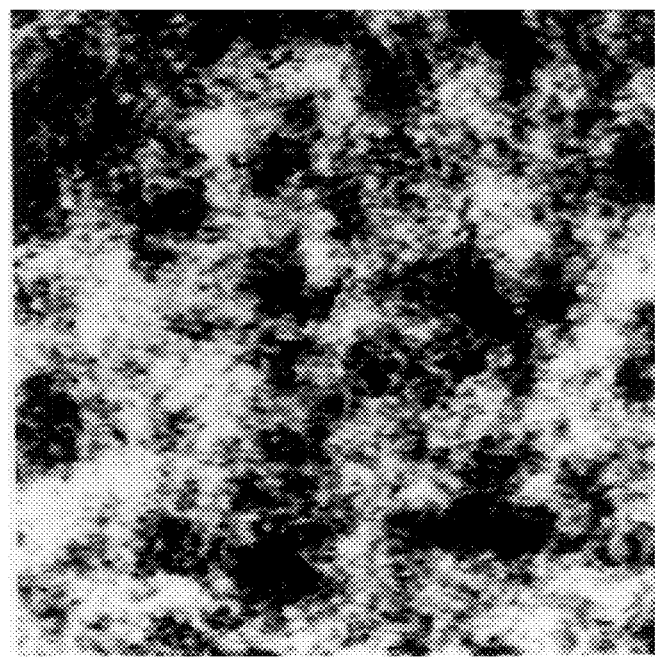
Figure 2:
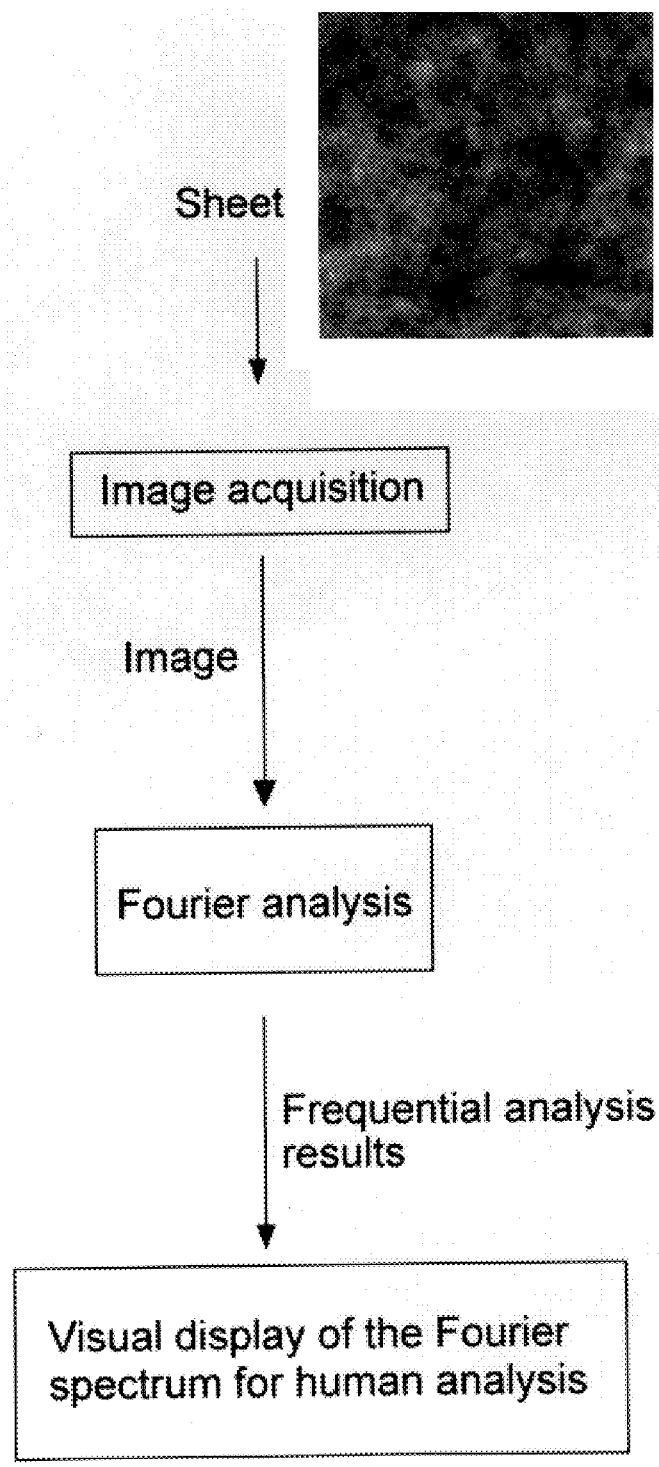
FIG. 2 is a flow chart of a prior art sheet image analysis method.
Figure 3C:
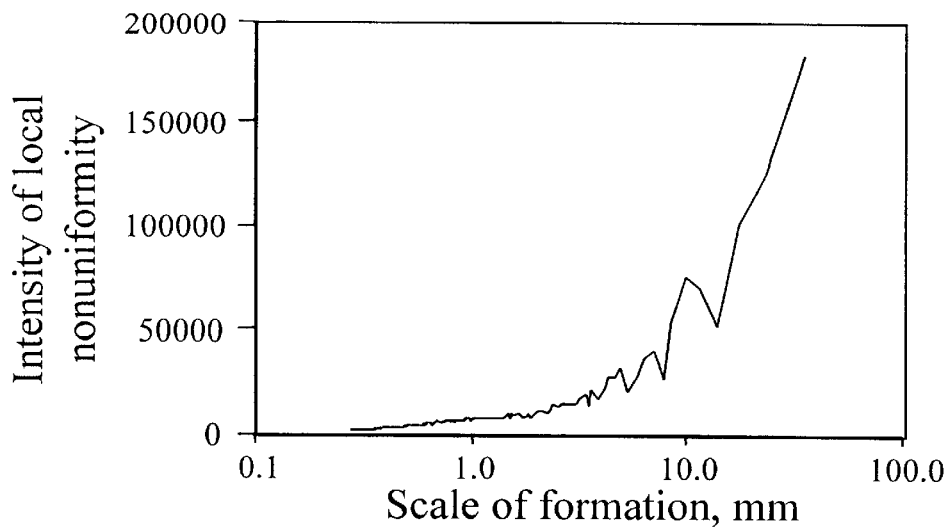
FIGS. 3c, 3d, 3e, 3f, and 3g are plots of intensity of nonuniformity versus scale of formation for raw image data, raw virtual paper, normalized data, smoothed data, and data within a selected range, respectively.

FIG. 3a illustrates the initial basic steps in the method according to the preferred embodiment based on a 2-dimensional FFT analysis and which processes the data in an original way. The image is acquired by a visible light transmission technique. A sheet is placed on a lightbox and its image is acquired with a commercial black and white, CCD video camera discriminating 256 grey levels.

Image processing is done using a computer. The computer program, described in more detail below, is written using the programming environment LabView from National Instruments. All image processing, management or analysis subroutines come from a commercially available image analysis software library named Concept VI, commercialized by GTFS Inc.

A square image is required for the further processing. A 256 by 256 pixel image is extracted from the original image. The real size of this 256 by 256 pixel image, which is the field of view of the equipment, is 60×60 mm. This size is a compromise between having a field of view large enough to provide information representative of the sheet, and the problem of maintaining uniform lighting over the field of view, more difficult the larger the field of view. This image is mirrored twice, in both vertical and horizontal directions, to produce a mirrored map which is therefore 512 by 512 pixels, as shown on FIG. 3b. The purpose of this mirroring operation is to adapt the data for the Fast Fourier Transform (FFT) treatment. As the Fourier transform of a set of data, on which the algorithm of the FFT is based, works efficiently only on periodic functions, distortion is introduced by the non-periodicity of the map of grey level of a sheet. The mirror operation is used for the purpose of reducing this effect. The image, 512 by 512 pixels, is then processed by the FFT subroutine. The result is a complex plane, a 2-dimensional square table having a dimension of 512 in both directions. The complex plane is treated in order to extract the amplitude plane. Thereby the amplitude of each number in the complex plane is processed, then placed in a new 512 by 512 table, which is the amplitude plane. The amplitude plane is then extracted from the power spectrum, expressed as frequency/amplitude curve.

The frequencies are converted to wavelength, according to the size of the original image, i.e. according to the field of view of the image used. As this wavelength relates directly to the dimension of the local nonuniformity in the plane of the sheet, it may be called the "scale of local nonuniformity", or, for the case of paper, the "scale of formation", millimeters. Thus the "scale of formation" is defined as the dimension of the square field of view of the image, multiplied by 2 due to the mirroring of the image, divided by the frequency of the frequential analysis, Therefore two data sets are produced, each of 256 data points. One set is for scale of formation. The other set is the mean amplitude of the power spectrum at each value of scale of formation, which is named the "intensity of local nonuniformity" of the sheet at a particular value of scale of formation. An example is FIG. 3c, which is named the raw Paper Formation Line.

Figure 3D:
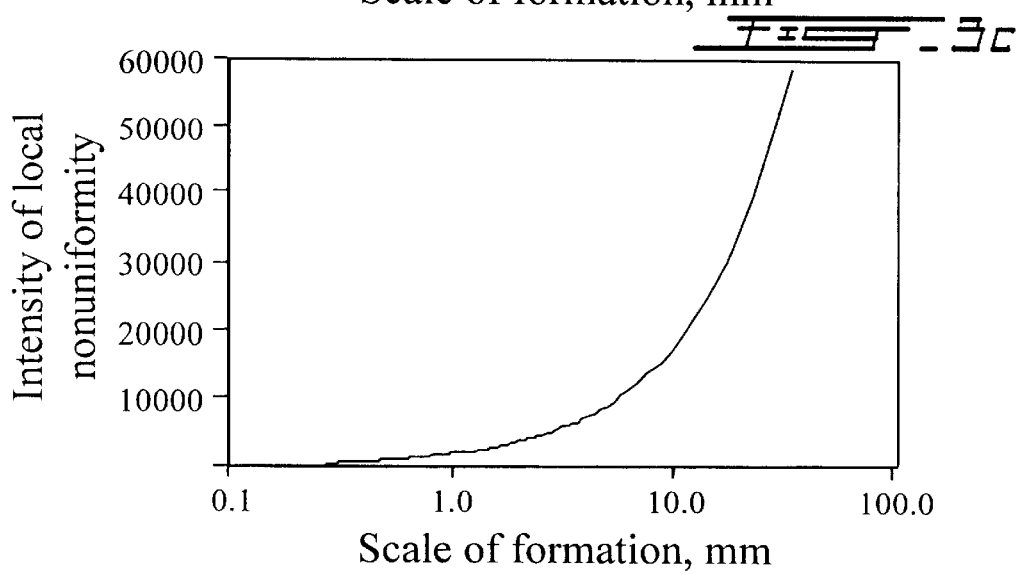
Figure 3E:
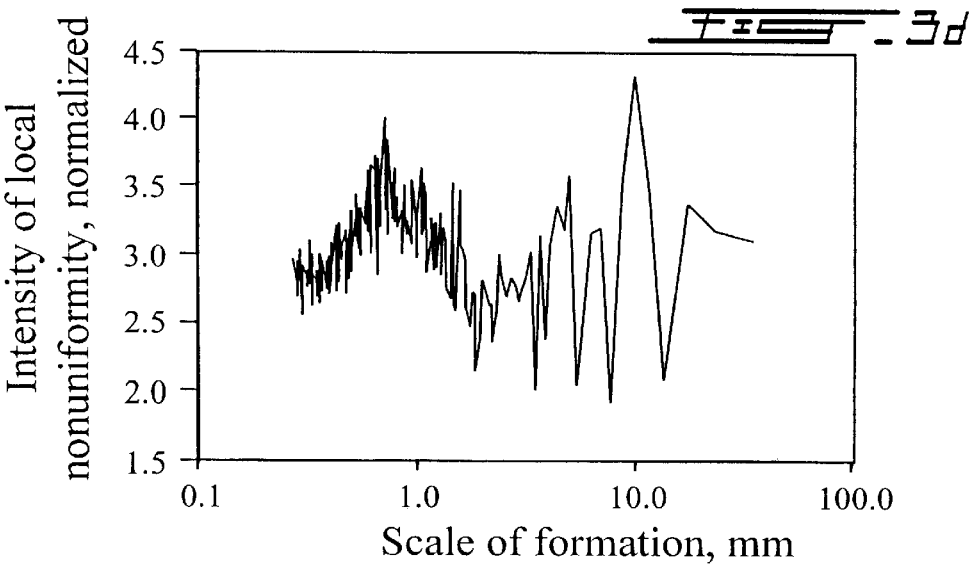

In the preferred embodiment, these raw values are normalized. For this purpose, a "virtual sheet" is used. This virtual paper sheet is a computer-generated data map, processed once only and stored for use as a standard which is designed to have a quality of formation better than any real paper (at least any real paper being manufactured by the paper manufacturing process used to make the paper being analyzed). The virtual paper is then processed a single time through the same data process used for every image of real paper, as documented above. Thus for the virtual paper, two data sets are produced, each of 256 data points, one set for the scale of formation, the other set for the intensity of local nonuniformity at each value of scale of formation. FIG. 3d shows the raw Paper Formation Line of the virtual paper. At each one of the 256 values of scale of formation the value of intensity of local nonuniformity for the sheet being examined is divided by the intensity of local nonuniformity for the virtual paper, thereby producing the value of normalized intensity of local nonuniformity for the sheet being examined. FIG. 3e shows this normalized Paper Formation Line. This normalizing is a simple operation for convenience, and could be omitted or other normalizing procedures could be used.

Figure 3F:
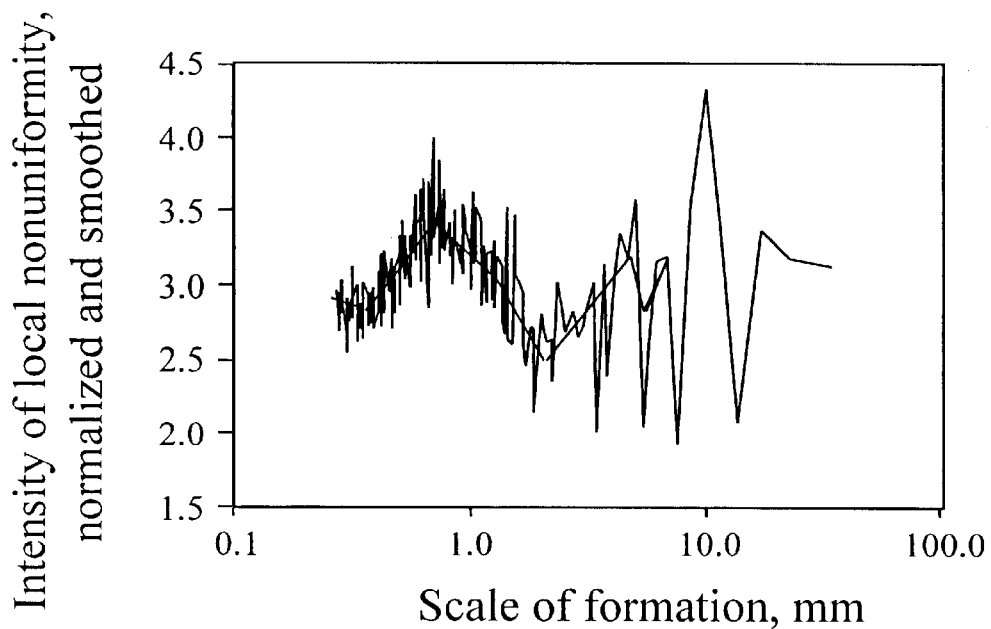

Scale of local nonuniformity or scale of formation derives from a wavelength, which is distributed highly nonuniformly on the scale of formation dimension. This results in an overly fine resolution at the lower end of scale of formation. It is practical to group values of intensity of local nonuniformity over selected regions of scale of formation in order to produce an average of the intensity of local nonuniformity over each such region of the raw Paper Formation Line. Thus the final set of values are of n intensities of local nonuniformity, normalized, at n values of scale of formation, with n being between 1 and 256, as shown on FIG. 3f. The value of n and the selection of which values of scale of formation to group together may be chosen freely by the user, as appropriate. The values of intensity of local nonuniformity at the n values of scale of formation selected may be displayed for the information of the user. When this is done for the demonstration case of paper as the sheet, in the form of the intensity of local nonuniformity, normalized, as a function of scale of formation, it can be termed the "final" Paper Formation Line.

Figure 3G:
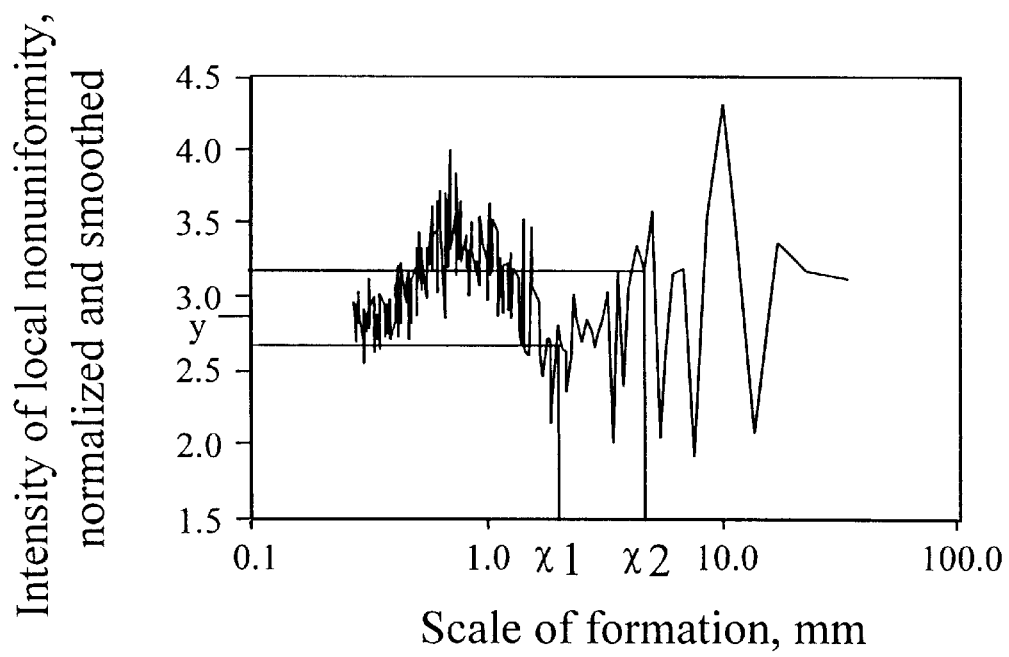

If the user has determined that for a particular case what is important is only the components of formation that occur over a specific range of values of scale of formation, then the above general capability can be used to produce the single value of intensity of local nonuniformity which applies over just that range of scale of formation. An example is FIG. 3g.

As may be seen from FIG. 3e, there is considerable variability in the Paper Formation Line, particularly at large scales of formation. This variability is inherent to the method. Thus one usually processes Paper Formation Lines from adjacent samples of the same sheet, then produces the mean Paper Formation Line of all these samples as being representative of the sheet. In the cases described below, from 4 to 10 independent, adjacent images per sheet were taken.

Having described the preliminary part of the data processing, examples of how this information can be applied, and how it needs to be processed in order to be used will now be described. FIG. 4 summarizes the uses explained below.

Figure 5A:
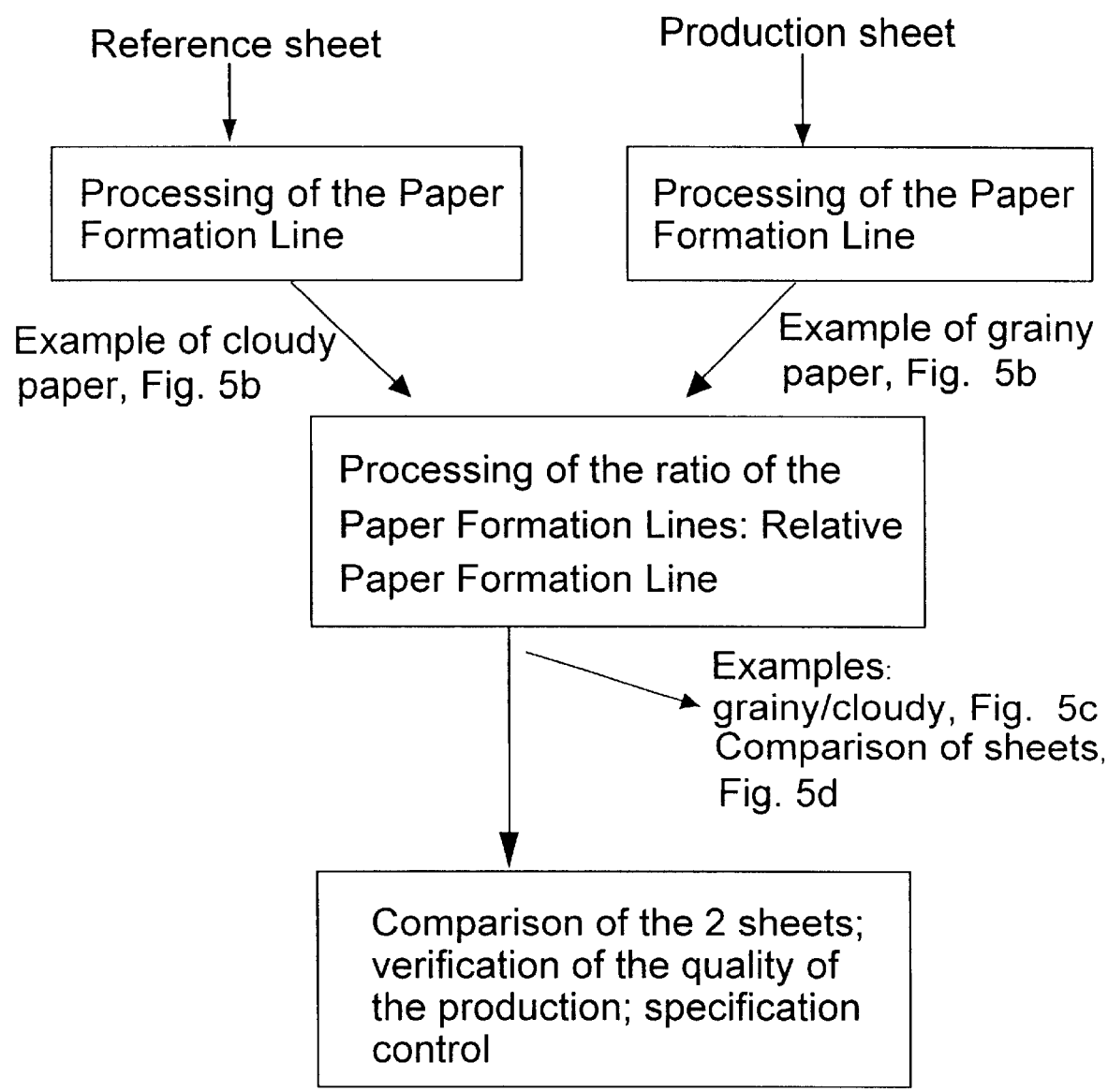
FIG. 5a is a flow chart representing the method of quality control according to the preferred embodiment.
Figure 5B:
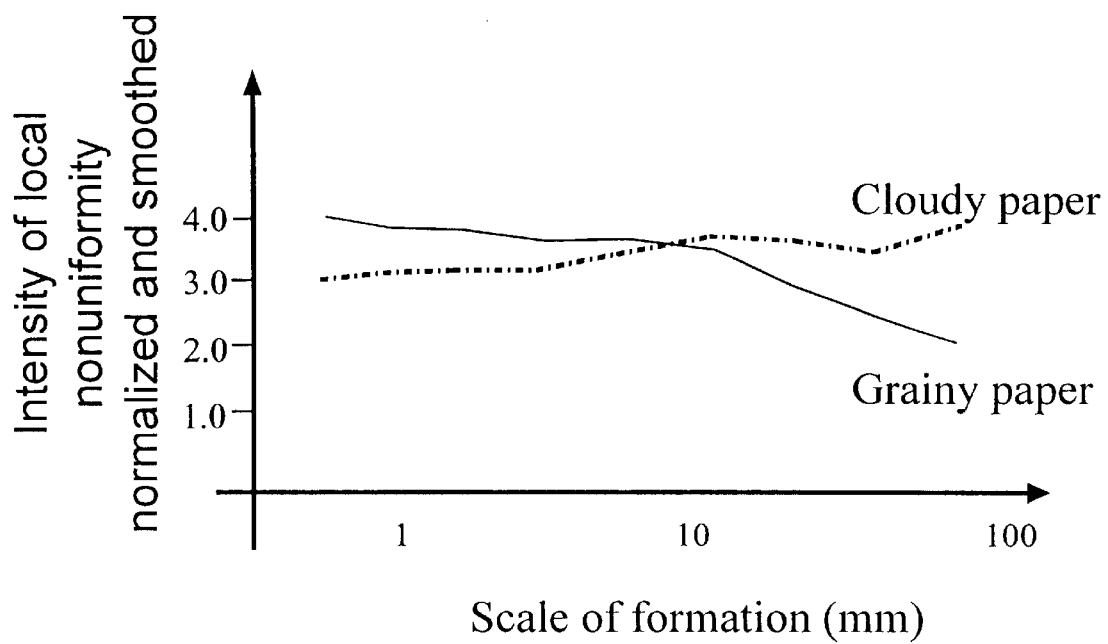
FIGS. 5b, 5c and 5d are plots of intensity of nonuniformity versus scale of formation for grainy and cloudy paper, grainy paper relative to cloudy paper (smoothed), and relative paper formation lines for five pairs of linerboard.
Figure 5C:
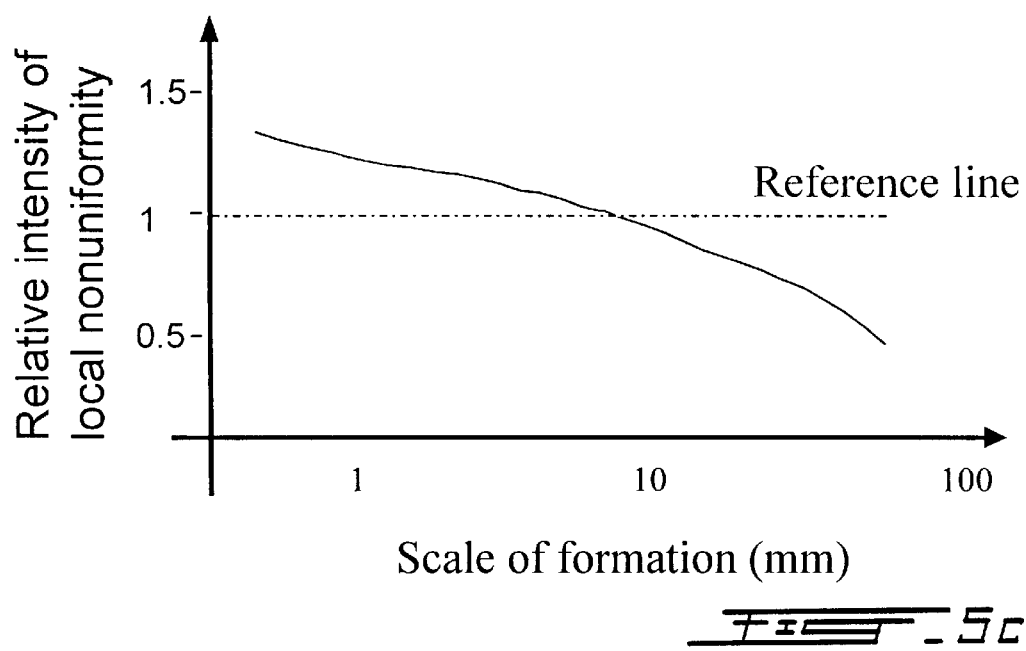
Figure 5:
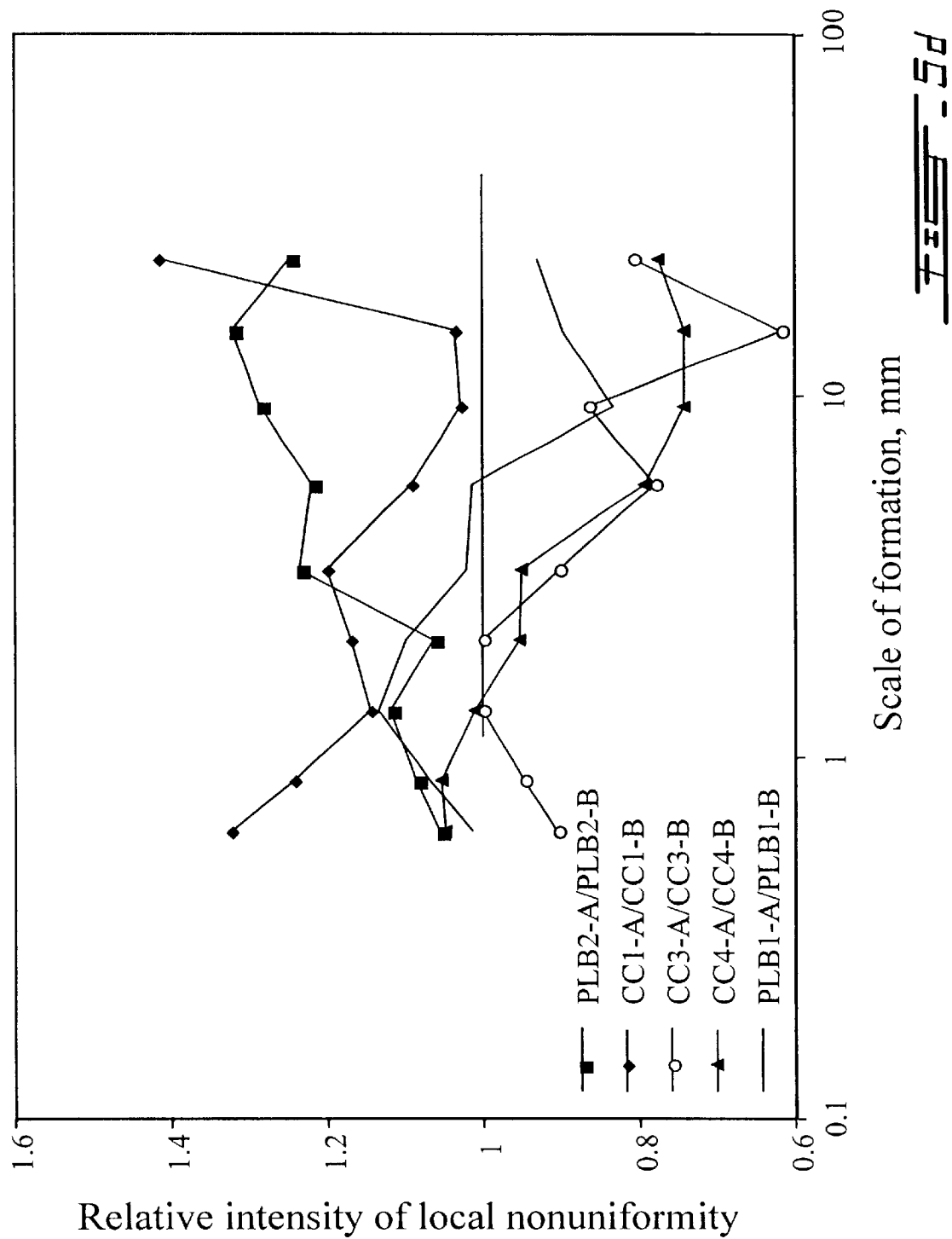

One use is for quality control of the sheet being produced, as schematized FIG. 5a. If the user has a high quality sheet, i.e. of low local nonuniformity of structure, such a sheet may be used as a reference sheet. For the case of the sheet material being paper, then the Paper Formation Line of any sheet being examined may be compared to the Paper Formation Line of this reference sheet in order to have a quantitative comparison of the local nonuniformity characteristics. The reference sheet could for example be the best quality paper of that grade ever produced on that papermachine, or the best quality paper of that grade on the market as produced by a competitor. An example is the previous cases of grainy and cloudy papers, FIG. 5b. At each value of scale of formation being used, the ratio of the intensity of local nonuniformity of the test sheet to that of the reference sheet may be calculated. When these relative values of intensity of local nonuniformity are displayed as a function of scale of formation, it is called the Relative Paper Formation Line, FIG. 5c for the example of grainy/cloudy paper quality. On this plot the value of relative intensity of nonuniformity equal to one corresponds to the test sheet having, at that scale of formation, the same intensity of nonuniformity as the reference sheet. Values greater or lesser than one correspond to the test sheet having an intensity of local nonuniformity, respectively, greater or lesser than that of the reference sheet. Thus the Relative Paper Formation Line shows, at each value of scale of formation, whether the test sheet is of poorer, the same, or better formation than the reference sheet. Without use of a specific reference sheet, the user may simply define a range of values for the Paper Formation Line as being its specifications or target values for the product.

This application can be used to differentiate sheets for which, as frequently occurs, papermakers and printers can distinguish by eye, but which are not distinguished or are distinguished poorly by current commercial formation test instruments. Not only can the method of paper formation determination according to the invention distinguish sheets now more sensitively, but it can determine in what way the formation of sheets are different. The Relative Paper Formation Line mode of operation of the present invention is particularly relevant for that purpose. FIG. 5d shows the results of the present Applicants' study done on linerboard produced on two similar papermachines, located side by side in the same paper mill, using identical furnish, operated by the same staff, producing nominally the identical grade of paper. In the case of all five pairs of sheets used in this test, one from each papermachine, the pairs of sheets were indistinguishable by the Kajaani formation test instrument, one of the commercial instruments currently used widely around the world. However each of these five pairs of sheets were distinguishable qualitatively through visual inspection by the company staff to an extent considered important for reasons of product quality. Each of the five pairs of sheets, of basis weight in the range 100–215 g/m$^2$, was examined using the preferred embodiment, and the five Relative Paper Formation Lines were produced by using one sheet of each pair as the reference sheet.

The Relative PFL for the five pairs of sheet is shown in FIG. 5d. In all five cases the sheet designated "B" is taken as the reference for the Relative PFL of the sheet designated "A".

Sheet PLB2-A is consistently worse than PLB2-B for all scales of formation, by a small amount for the smaller range of scale of formation but with a difference up to 30% at the large end of the range of scale of formation.

The pair designated CC1-A and CC1-B displays the opposite trend, i.e. the difference in formation nonuniformity between the two sheets is maximum at a large scale of formation, CC1-A being up to 40% worse than CC1-B, but at a scale of formation about 10 mm, the difference in nonuniformity of structure of the sheets is very small. These results indicate that if the papermaker is interested in properties which are related to the scale of formation in the range 7 to 15 mm, then the two sheets may probably be considered as identical, but if the properties of importance depend on scale of formation either below 5 mm and above 20 mm, then there is a very significant difference between the sheets.

For the third case, CC3-A and CC3-B, FIG. 5d shows that CC3-A is slightly better up to a scale of formation of about 5 mm, but then becomes much more better than CC3-B, with a difference of 30% in the quality of formation. In this case, if the papermaker is concerned with a property which is dependant on the 0.5 to 2 mm range of scale of formation, then these papers are similar; if the papermaker is concerned with a property which is dependent on scale of formation larger than 5 mm, then CC3-A is better than CC3-B, by up to 30%, and the related properties may therefore be quite different. This pattern is exactly the opposite of that found for the previous pair, CC1-A / CC1-B.

The first three cases show a behavior where one sheet is consistently better than the other by amounts which vary in different ways with scale of formation. The last two cases show a more complex behavior yet, with the Relative PFL crossing the value of 1.0. Occurrence of such a crossover means that over some range of scale of formation, one of the sheets is of better formation, while over another range of scale of formation the situation is reversed. In the case of the CC4-A / CC4-B pair, CC4-A is slightly worse than CC4-B up to scale of formation of about 1.5 mm, but then at a larger scale of formation CC4-A becomes better than CC4-B, by up to 25%. This substantial difference means that the paper for these two production lots has very different nonuniformity of structure, which would make the paper properties quite different. It is interesting to recall that the current commercial formation test instrument used by the paper manufacturer is unable to differentiate any of these five pairs of sheets.

Most striking of all is the fifth case, PLB1-A and PLB1-B, where paper PLB1-A is of worse formation up to a scale of formation 9 mm, above which PLB1-A becomes the better sheet. These differences are high, up to 20% worse, then 20% better. This behavior means that, depending to the use of the paper, either production lot may be the better quality paper. Thus the tests conducted of the utility of the present invention shows that the reality of sheet formation is such that old concepts of "better" or "worse" formation are quite inadequate approximations of a more complex reality. This example shows that the technique according to the present invention, which provides the information on the components of the formation over a wide range of scale of formation, has unique ability to evaluate paper formation in a clearly understandable way, and in a way that can be used by the papermaker as a basis of controlling the production process, as is detailed below.

It will be apparent to the skilled reader that two important advantages are provided by the implementation of the present invention. First, the technique is advantageously sensitive, having now been demonstrated to distinguish between pairs of sheets that papermakers know visually to be different but which are not distinguished by a reputable commercial test instrument. As the invention detects differences in the local nonuniformity of formation by up to 40%, its exceptional sensitivity is clear. Second, the technique is not only able to distinguish the sheets as different, but shows which components of formation are different, in which range of scale of formation, and by how much. These findings thus demonstrate both the great sensitivity of this method compared to current determination of formation, and its ability to reveal the impressive diversity of ways in which the formation of similar sheets are in fact different, Another application of the present invention relates to the CD (cross-direction) control of a papermachine, as shown schematically on FIG. 6a. As paper is produced on sheets up to about 10 meters wide, it is crucially important to maintain the quality of formation across the width of the sheet as uniform as possible. By determining the Paper Formation Line of the sheet at different CD positions, the papermaker can follow the stability of the CD profile of the machine and be guided thereby in taking appropriate corrective action when required.

Figure 7A:
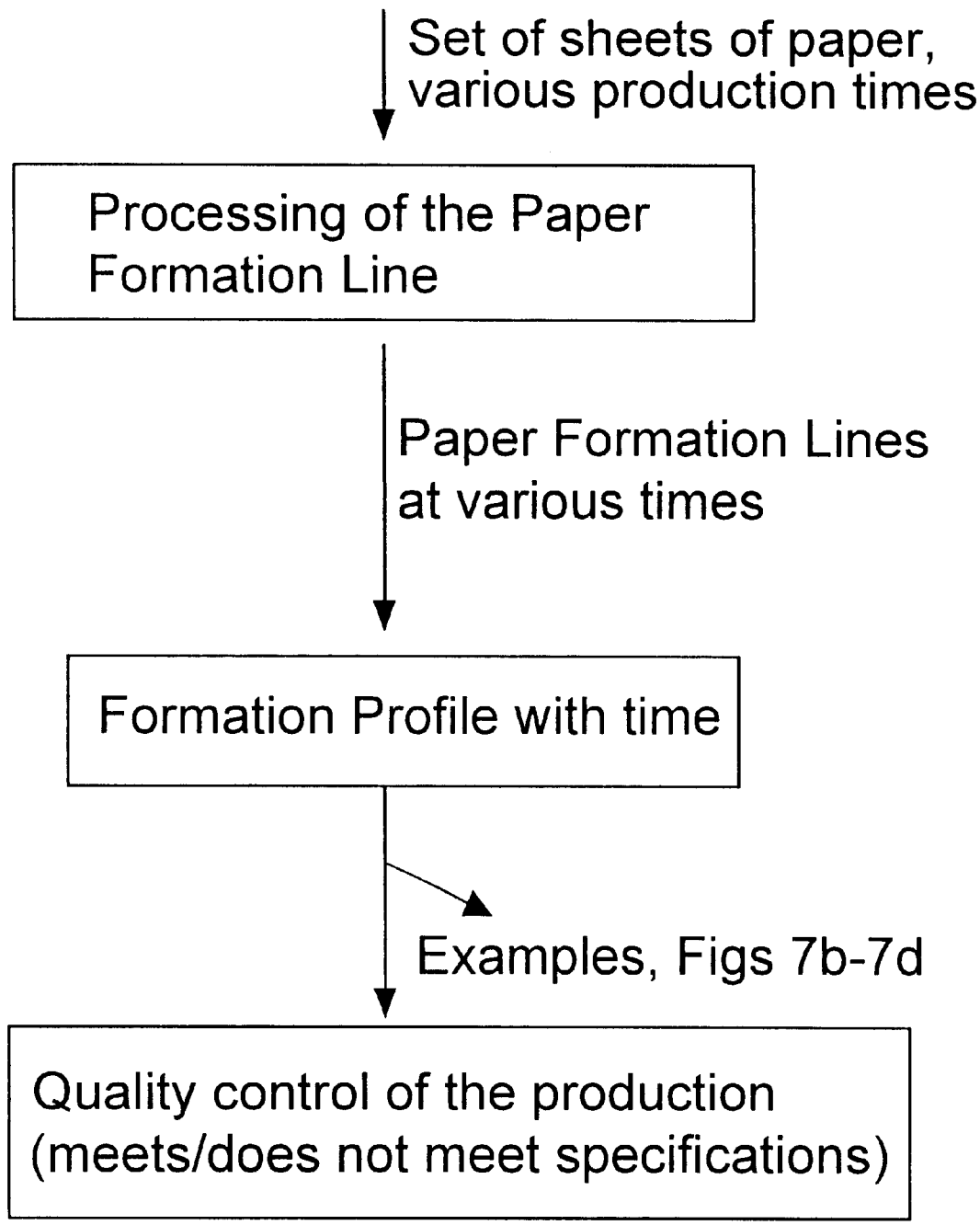
FIG. 7a is a flow chart representing the method of time control of paper quality according to the preferred embodiment.

As the user may follow as well the evolution with time of the quality of paper formation in the papermachine, the present method may be used for control of the operation of a papermachine over time, as shown on FIG. 7a.

Figure 6A:
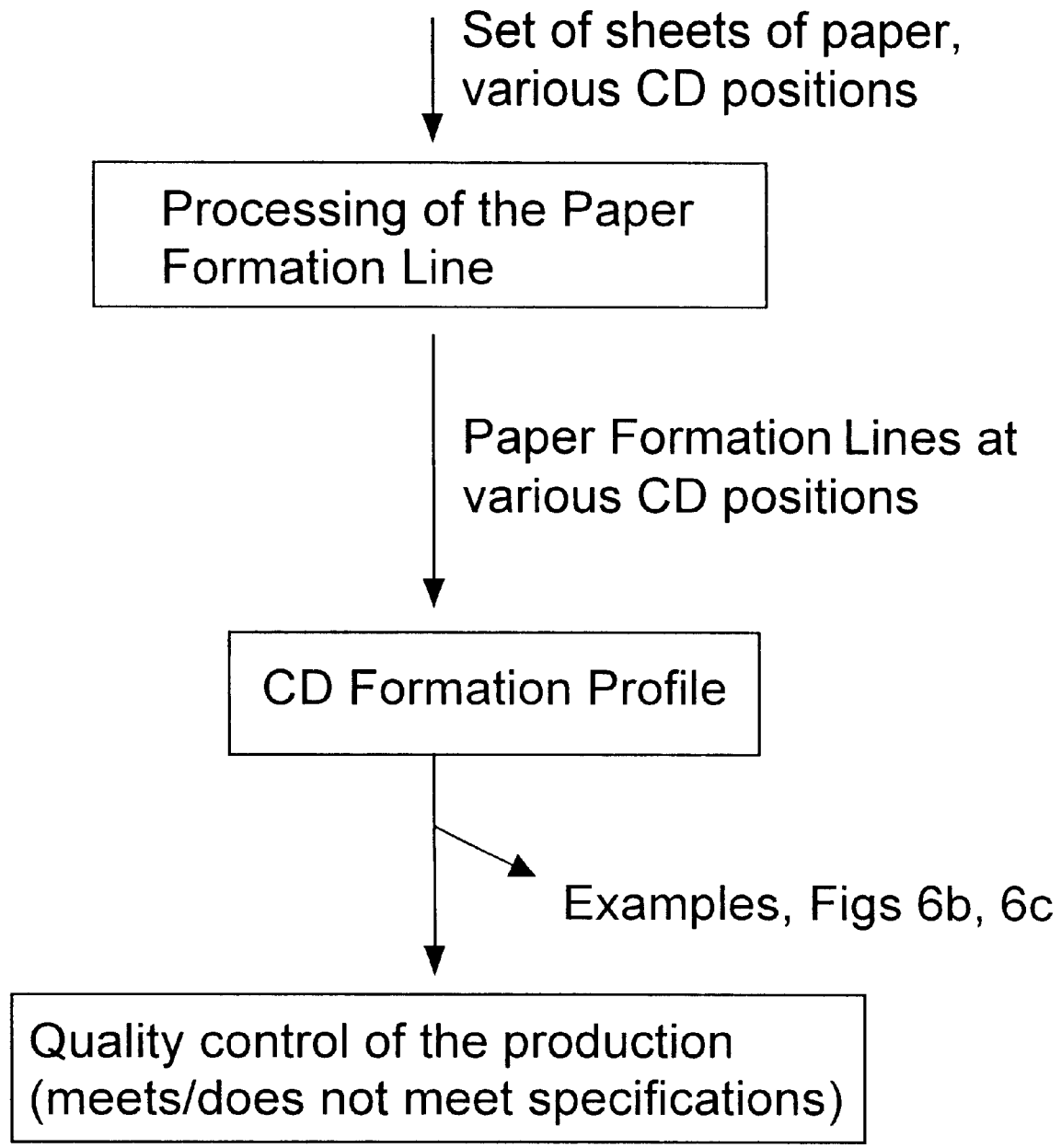
FIG. 6a is a flow chart representing the method steps of cross direction (CD) quality control according to the preferred embodiment.

Application of the method according to the invention to the problem of stability of paper quality over time and CD position, as described on FIG. 6a and 7a, has been demonstrated through a study carried out with a linerboard machine. This study was done with a 400–500 tons per day papermachine producing a premium grade of linerboard used to carry high quality printed images. The CD variability of formation was documented by monitoring five CD positions: the machine centerline position, each edge, and the two positions mid-way between the centerline and the edges. Five grades of linerboard, with basis weight from 139 g/m$^2$ to 282 g/m$^2$ were worked with. From the production of each of these grades during the July to October 1997 period, samples were obtained from at least two days, and for one grade, samples over three days. Thus samples of paper from 11 production dates, of five grades of linerboard of different basis weight were examined. With this plan it was possible to study first the CD variability of formation as a function of scale of formation within a given grade and production day. Secondly, for each of these five grades it was possible to document, over two or three production dates within a five month period, the evolution with time of CD variability of formation and CD average formation.

Figure 6B:
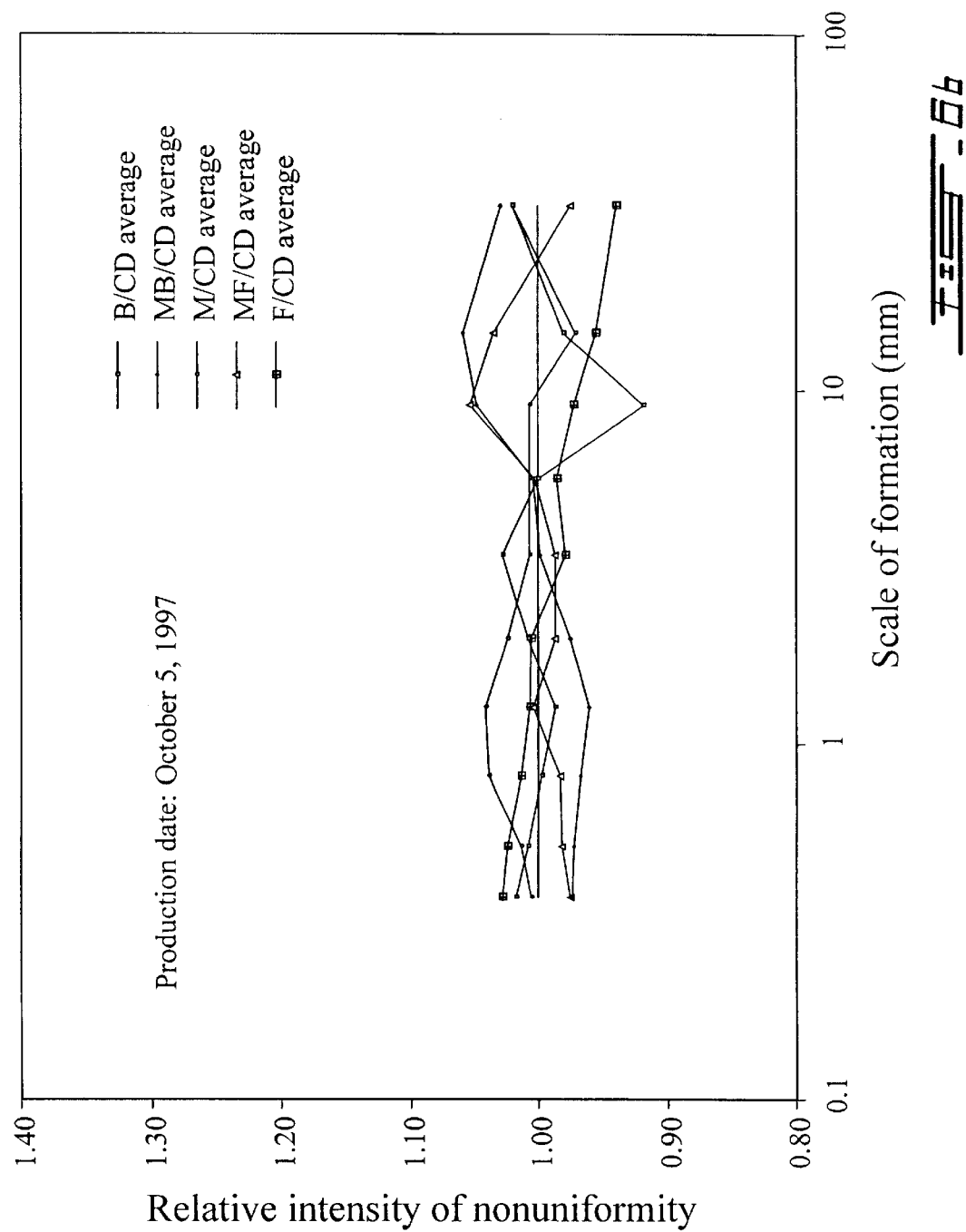

For the study of CD variability just the extreme cases are presented herein. The Paper Formation Lines of each of the five CD positions (Front, Middle-Front, Middle, Middle-Back, Back abbreviated on the Figure as F, MF, M, MB and B) are processed. Then the Relative Paper Formation Lines for each of these five positions are calculated, using as reference the mean value of the five CD positions. FIG. 6b and 6c show these results. Each Relative PFL represents one of the five positions. A value of the Relative PFL below 1 means that this CD position has a better formation than the sheet average; a value above 1 indicates that this CD position has a worse formation than the sheet average. With ideal operation there would be no dispersion in the CD dimension, i.e. with the 5 Relative Paper Formation Lines together at value of 1, showing that all the positions have exactly the same quality of formation. FIG. 6b shows the best of all cases evaluated. No Relative PFL for a specific CD position shows formation even as much as 7% different than the CD average at any value of scale of formation over the very wide range from 1 mm to 33 mm. Expressed alternatively, the poorest formation was always within 14% of that at the CD position of best quality formation for the components of formation over the entire range of scale of formation from 1 to 33 mm. FIG. 6c shows the worst case found, with formation for the two outside CD positions, Front and Back of the papermachine, being from 7% to 15% worse than the CD average formation, and this over a wide range of scale of formation from about 1 mm to 33 mm. In this case the CD position of poorest formation quality has then about 30% more nonuniformity of structure than at the best CD position, indicating the need for action to improve the papermachine operation substantially.

Figure 7B:
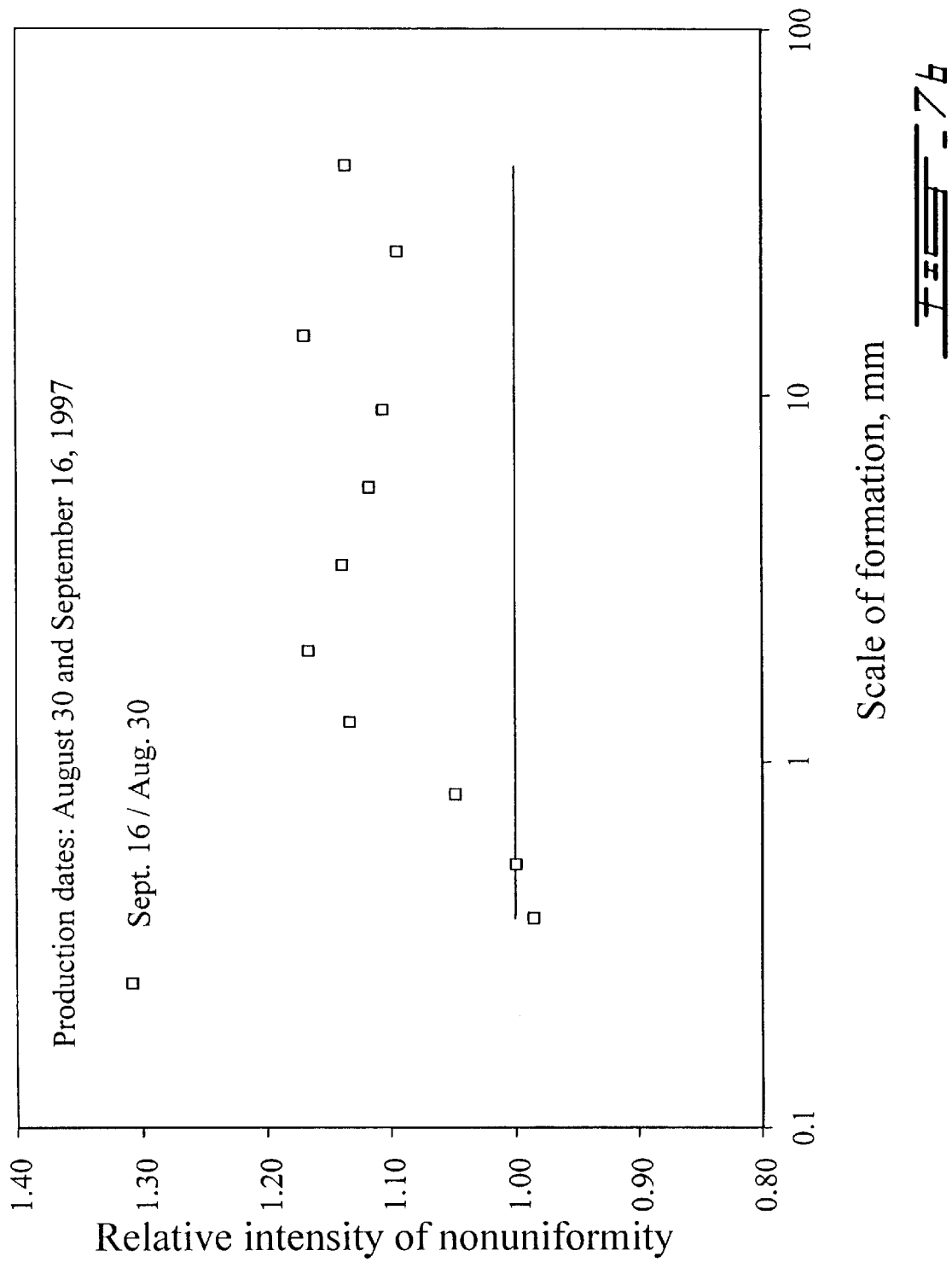

For the time evolution of paper formation, three representative cases of the six that were studied are discussed herein. For each Relative PFL, the above defined CD-average Paper Formation Line for the earlier production date are used as the reference. The only simple case is that for the 139 g/m² grade, for which the time evolution, exceptionally, is straightforward. FIG. 7b shows that from August 30 to September 16 the CD mean quality of formation simply deteriorated over most of the range of scale of formation. On the latter production date the average nonuniformity of structure over the wide range from 1 to 33 mm scale of formation was worse by from 10% to 17%.

Figure 7C:
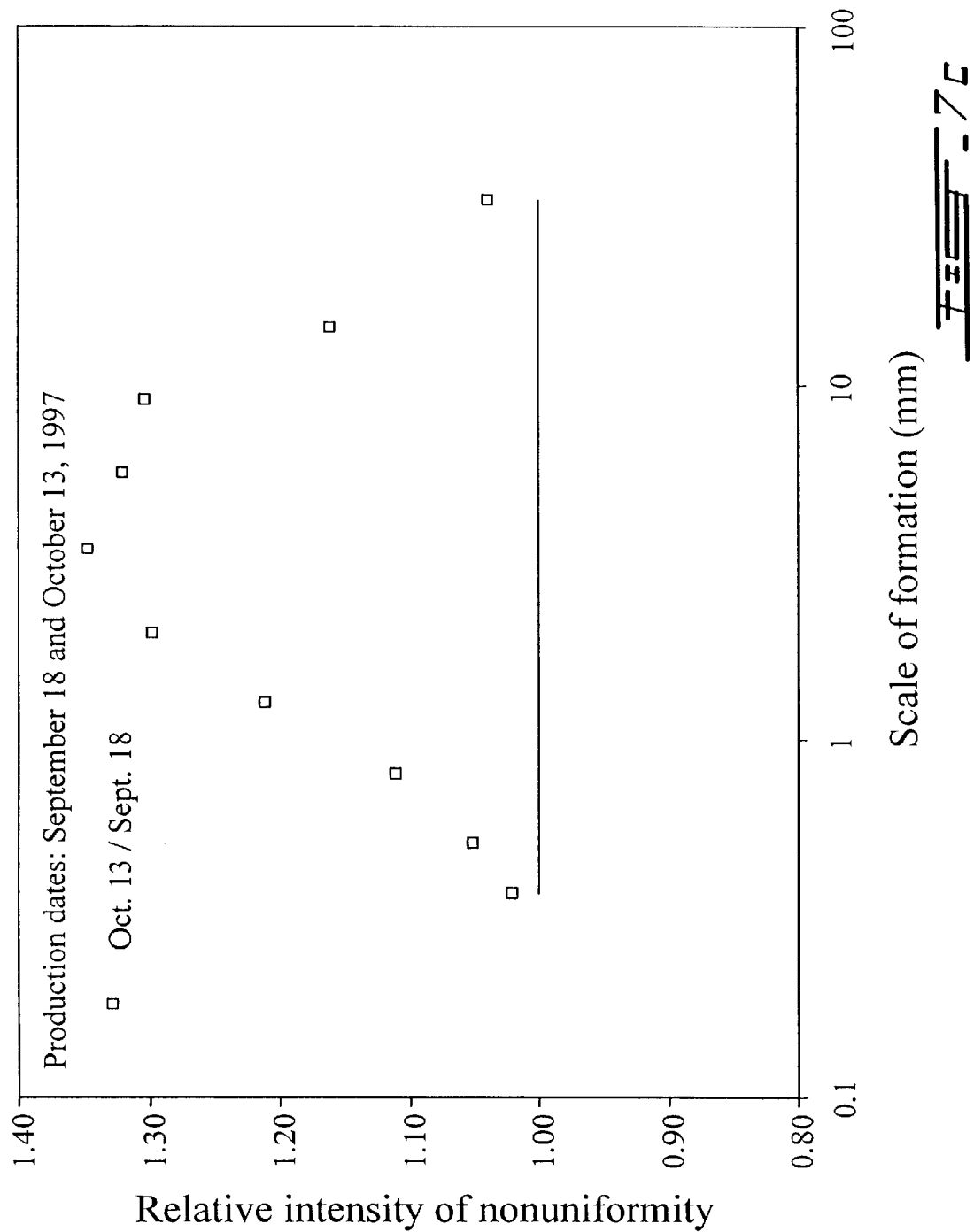

The results for the 199 g/m² linerboard are particularly meaningful because between the two production dates a papermachine adjustment was made with the specific objective of reducing the CD variability of formation. FIG. 7c shows however that what actually took place was that the CD average quality of formation was decidedly worse after the adjustment, becoming poorer over the entire range of scale of formation, by as much as 30–35% worse over the intermediate range of scale of formation from 2 to 10 mm. The results for formation nonuniformity at the five individual CD positions for the 199 g/m² linerboard, analogous to those shown on FIGS. 6b and 6c, establish that it was high nonuniformity of formation at three positions (at the front and back of the papermachine and at the centerline) which resulted in the large degradation in CD-average quality of formation for this papermachine adjustment as documented on FIG. 7c. Thus the greater sensitivity of the formation measurement technology according to the invention not only showed the overall deterioration in quality of formation, contrary to expectation, but shows which components of formation were most affected by the change, i.e. those in the range of 2 to 10 mm scale of formation. None of these findings could be revealed by current formation measurement technology. Combining the nature of the change that was made to the papermachine with the effect of that change enables addressing effectively the problem of reducing CD variability of formation.

For the 282 g/m² linerboard, FIG. 7d, data from three production dates is shown. For this case, one sees a mixed behavior in the trends with time for quality of formation. Formation nonuniformity for the entire range above about 2–4 mm scale of formation got worse with time: much worse (by up to almost 40%) on August 1 than June 27, and moderately worse (by up to about 10% on October 5). By contrast, for the range below that 2–4 mm dividing point on scale of formation, the local nonuniformity of formation got better with time, by up to 10%–15% better. This graph strikingly illustrates the importance of distinguishing quality of formation according to scale of formation. This evolution is an example of the common case for which there is no answer to the question as to whether the quality of formation got better or worse. In this case, the quality of formation actually did both. Quality of formation got better in the range of scale of formation below about 3 mm, and it got worse for scale of formation above 3 mm.

The above described study of the CD profile of formation and of the evolution of formation with time provide demonstrations of the usefulness of the technique according to the invention. This technology provides unique information as to how the formation of the paper over time and at different CD positions is characterized sensitively and with the components of nonuniformity revealed. This information can help the papermaker in tuning the production process in order to stabilize sheet structure over time and with respect to CD position across the machine, and do so at a level of quality not previously achievable.

According to the invention, the method of determining the local nonuniformity of paper structure may be used to control of the papermaking process, as shown in FIG. 8. First, the effect that the parameters in the process of manufacturing paper have on the components of paper formation are determined. One thereby establishes over which range of scale of formation each parameter acts and how important is that effect. The operator can then use this information to tune the papermaking process parameters in order to optimize the particular paper properties of greatest commercial value and to maintain this high quality product over time and CD position.

Paper formation is not only of interest by itself, but is also important because it affects print quality, paper strength properties, coatability, visual quality and other key quality parameters of paper. The relationship between these properties and the components of paper formation as a function of scale of formation was unknown prior to the present invention. It is thus possible to use the invention to estimate paper properties, shown schematically in FIG. 9a. Paper quality is characterized by, and its market value influenced by, paper properties such as strength properties, mechanical properties, its coatability, its printability. However, measurement of these properties may be time-consuming and expensive. As these properties may be greatly affected by formation, the correlation between paper formation and paper properties has long been of practical interest. The objective is to be able to estimate these properties efficiently by measuring formation in order to minimize the number of direct measurements of these many properties. Since factors other than formation affect these properties to a greater or lesser extent depending on the particular property, what is achievable is an estimation of these properties. The precision of so doing depends on how high the correlation is between paper formation and each paper property.

The method according to the invention provides an efficient way to predict the paper properties by study of the Paper Formation Line. As a first step, a set of sheets of paper, for which the property of interest has been measured, is analyzed. The Paper Formation Line is produced, for each sheet. Then, for the entire set of sheets, the property is correlated with the component of formation for each selected scale of formation. The $R^2$ value is processed. If there is a region of scale of formation which has an effect on the property, then the $R^2$ correlation will be higher for the values of scale of formation inside this region. Thus one determines two things: (1) what is the range of scale of formation for which the $R^2$ is high, which gives the range of scale of formation that determines this specific property, and (2) what is the value of the $R^2$ over this range of scale of formation, which gives the strength of the correlation of this paper property, for this type of paper, relative to the local nonuniformity over the controlling range of scale of formation as determined in (1).

The $R^2$ correlation values between formation index and offset print quality of uncoated fine paper are low, at 0.22, 0.32, 0.375, each $R^2$ value corresponding to use of the formation index given by a different current commercial formation test instrument. The low values of these $R^2$ values and the substantial differences between the results obtained with different instruments indicate that formation is measured very inadequately by the technology of current formation instruments. All these instruments produce a single number as an index of formation, a procedure which is inherently incapable of describing the distribution of local nonuniformity across the sheet, an essential characteristic of its formation structure.

Figure 9A:
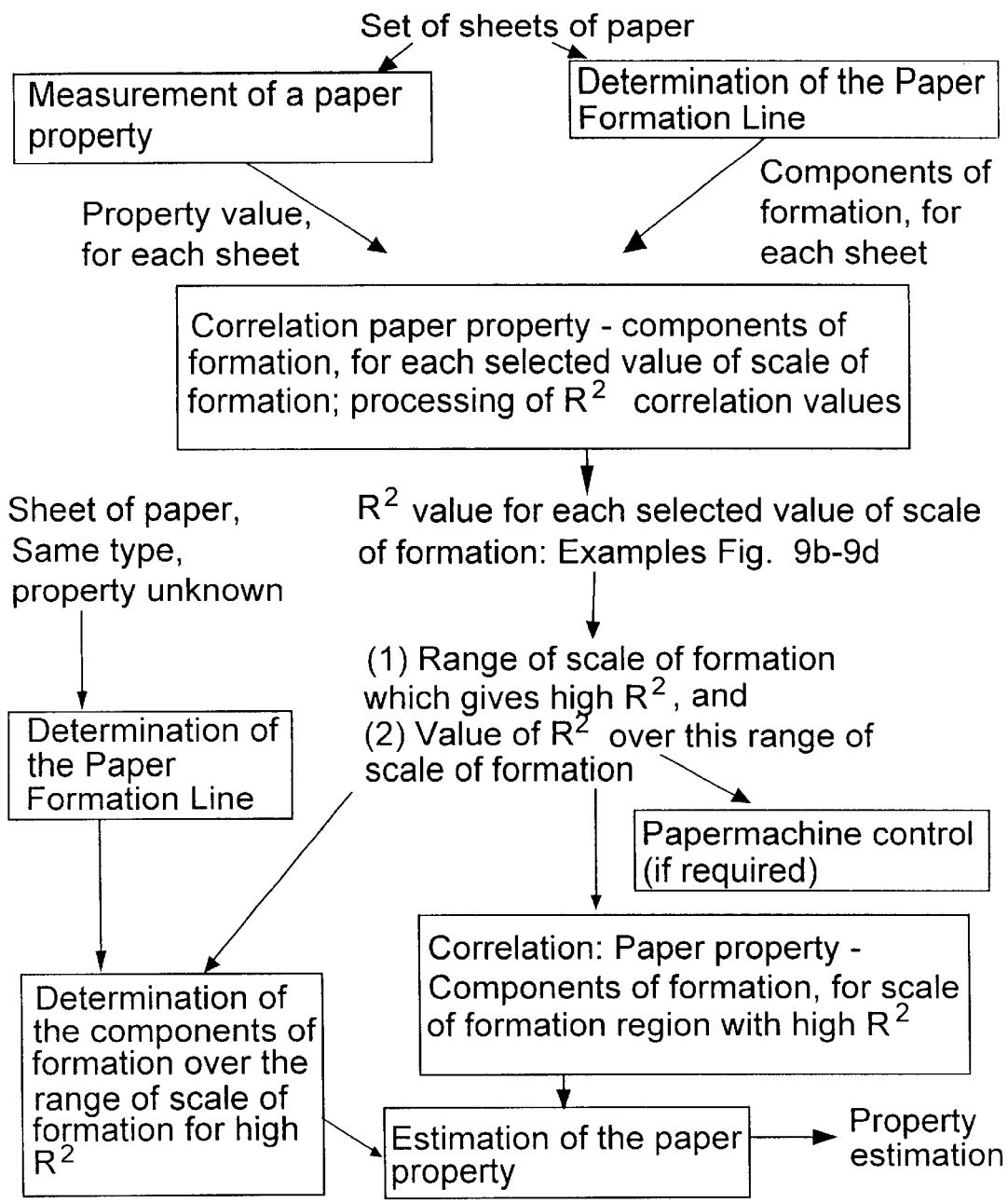
FIG. 9a is a flow chart representing the method of paper property estimation according to the preferred embodiment.
Figure 9B:
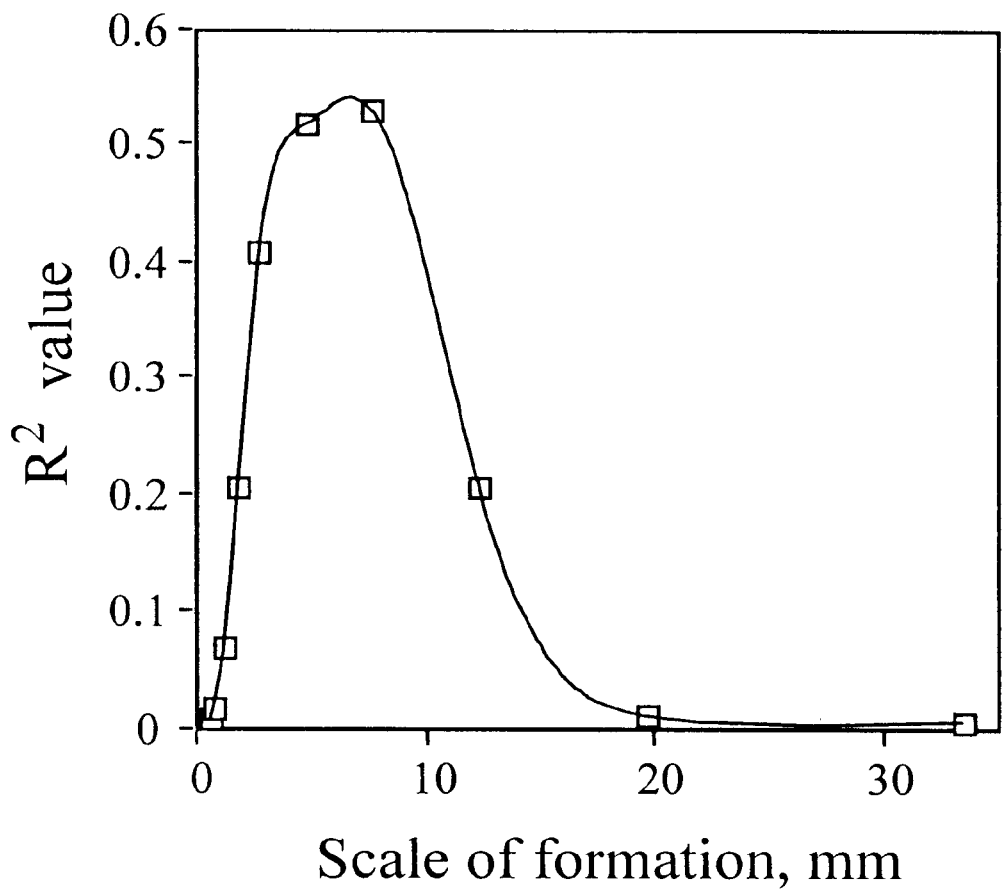

FIG. 9b shows the results of another test involving 32 sheets of uncoated fine paper, 72–103 g/m², from a variety paper companies, for which the quality of the printing under commercial conditions on a Heidelberg Speedmaster four color offset press, was determined by an all-pairs ranking of evaluations made by 34 printers. These results indicate which components of formation are important for controlling off-set print quality of uncoated fine paper, these being the components giving high $R^2$ correlation values on FIG. 9b. It can be seen that the components of formation below 2 mm or above 10 mm scale of formation have negligible effect on print quality. The components of formation for scale of formation between 4 and 8 mm have a strong determining effect on print quality and are thereby revealed to be the components of formation nonuniformity important in this paper property-paper type case.

The extent of control of this paper property by the components of formation in the range of scale of formation having been determined as important is calculated. Over the range of scale of formation of 4 to 8 mm, it has been found that the $R^2$ correlation value between print quality and intensity of local nonuniformity of paper structure is 0.56. As it is well known that print quality is influenced by a number of variables in addition to the quality of paper formation, such as variability in the printing process and in surface properties of the paper, it is interesting that over half (56%) of the variability in print quality derives from a sole source, i.e. the components of formation in the range 4 to 8 mm scale of formation. By contrast, the $R^2$ values for the formation index-print quality correlation for three current formation test instruments (0.22, 0.35, 0.375) averaged 0.31, about one half of the 0.56 value.

These test results show that paper formation, when determined appropriately using the present invention, has about double the effect on offset print quality of fine paper as that shown by current formation test instruments.

The carrying out of a print quality study according to the prior art can take months. Using the present invention, one can determine within seconds the components of formation which have high correlation with the print quality. Thus papermaking process conditions may be adjusted so as to produce paper which will give the best printability achievable, by improving the key components of formation.

By contrast, when the operator now changes papermaking parameters which improve formation as indicated by current formation test instruments, an improvement in printability is expected, but may not occur. This is because for offset printing of fine paper it is only the components of formation in the 4 to 8 mm range of scale of formation that can improve print quality. If the changes made improve the quality of formation in the range below 4 mm or above the 8 mm value of scale of formation, the quality of formation will have improved, but the test results show that printability would not improve, or may even be worse, because one has not improved the components of formation which control offset print quality, i.e. in the 4 to 8 mm range of scale of formation. Hence results based on the overly simple way by which formation is measured by current test instruments may be quite useless in the objective of improving the printability of the product.

A further application of the present invention concerns the dependence of a mechanical property, tear strength, on the quality of paper formation. In a manner similar to that of what described above for print quality, samples of commercial newsprint and measurements of its tear strength were tested. The newsprint used was a standard grade, 48–49 g/m² basis weight. As tear strength of paper is a direction-dependent property, the study was carried out for tear strength in both the machine direction (MD) and the cross-machine direction (CD) of the paper. FIGS. 9c and 9d show these complete results.

For the tear strength of newsprint in both the MD and CD directions, the components of formation below about 10 mm and above about 25 mm scale of formation have little effect, and it is the components of formation between scale of formation about 10 and 25 mm that control this property. Regarding the extent of control of tear strength of newsprint, it is identified by the formation in the 10 to 25 mm range of scale of formation that was determined above to be important. Specifically, over this range of scale of formation, the $R^2$ correlation values are 0.63 for CD tear strength and 0.78 for MD tear strength. As tear strength is also affected by factors other than formation, such as parameters in the process for producing the mechanical pulp, it is impressive that the components of formation determined to be important do in fact account for from about ⅔ to ¾ of the variability in MD and CD tear strength of newsprint.

The results of the correlation may be used as well for property estimation. As one determines what is the range of scale of formation for which the components of formation have a strong effect on the property of interest, one then correlates the property with the components of formation for this specific range. The curve so obtained may then be used for estimating the property of a sheet without measuring the property, just by processing the component of formation at the specific range for this sheet and retracing the value of the property on the correlation curve.

For three different test cases, it has been shown that there is typically only a narrow range of scale of formation for those components of formation which control a particular paper property. In one of these cases the grade of paper was uncoated fine paper and the paper property was offset print quality. In the other cases the grade of paper was newsprint and the paper properties were MD (machine direction) tear strength and CD (cross direction) tear strength. There was no overlap between the narrow range of the relevant range of scale of formation important for the first case with that important for the subsequent cases. For a given type of paper, and a given property, such a study provides both the critical range of scale of formation in which the property is sensitive to formation, and the level of the correlation between that property and the components of paper formation in this relevant range. Thus it is subsequently possible to estimate the property by the method of measurement of sheet formation according to the invention, the precision of this estimate being given by the level of the correlation between paper formation and this property.

The sample applications described above are distinct, but may in practice be associated in a variety of ways. For example, the CD control of the papermachine and the time control of the papermachine are likely to be used together. The papermaker may use the results of the present method for estimating paper properties and would also use this information as the basis of adjusting the papermachine when specific paper property specifications are not being met.

The control of the manufacturing process, FIG. 8, and the estimation of specific sheet properties, FIG. 9a, both require preliminary work to determine how the manufacturing process parameters affect the components of formation, and which components of formation are relevant to specific paper properties. However the objectives of quality control, FIGS. 5a, 6a and 7a, and differentiation between sheets, FIG. 5d, may be carried out directly, with no preliminary study.

It is to be understood that the above detailed description of a preferred embodiment has been provided herein in explicit detail for the purposes of teaching the present invention and is not intended to limit the scope of the present invention as defined by the appended claims.

We claim:

1. A method of determining a quality of sheet material comprising steps of:
   acquiring an image of a portion of a surface of said sheet material;
   analyzing said image to determine an intensity of local nonuniformity in said image as a function of a scale of formation;
   selecting a predetermined range of said scale of formation responsible for determining said quality; and
   generating an output value indicative of said sheet material quality from said intensity of local nonuniformity within said range;
   wherein said analyzing and said generating comprise non image-based analysis.

2. The method as claimed in claim 1, wherein said step of analyzing comprises conducting a Fourier analysis of said image.

3. The method as claimed in claim 2, wherein said step of analyzing comprises mirroring said image and calculating a discrete Fourier transform on said mirrored image.

4. The method as claimed in claim 3, wherein said sheet material is unprinted paper.

5. The method as claimed in claim 4, wherein said image is acquired using a lightbox and a CCD camera, said portion of said surface being approximately 6 cm by 6 cm.

6. The method as claimed in claim 1, wherein said sheet material is unprinted paper, and said predetermined range is selected such that said quality is graininess.

7. The method as claimed in claim 1, wherein said sheet material is unprinted paper, and said predetermined range is selected such that said quality is cloudiness.

8. The method as claimed in claim 1, wherein said sheet material is unprinted paper, and said predetermined range is selected such that said quality is cross-direction strength.

9. The method as claimed in claim 1, wherein said sheet material is unprinted paper, and said predetermined range is selected such that said quality is machine direction strength.

10. The method as claimed in claim 1, wherein said sheet material is unprinted paper, and said predetermined range is selected such that said quality is print quality.

11. The method as claimed in claim 1, wherein said sheet material is printed paper, said method determining a quality of print on said paper.

12. A method of quality control analysis of sheet material compared with respect to a reference sheet comprising steps of:
   acquiring a first image of a portion of a surface of said reference sheet;
   analyzing said first image to determine an intensity of local nonuniformity in said first image as a function of a scale of formation;
   acquiring a second image of a portion of a surface of said sheet material;
   analyzing said second image to determine an intensity of local nonuniformity in said second image as a function of a scale of formation;
   normalizing said intensity of local nonuniformity in said second image with respect to said intensity of local nonuniformity in said first image to obtain a normalized sheet material formation line output data set.

13. The method as claimed in claim 12, wherein said steps of analyzing comprise conducting a Fourier analysis of said first and second images.

14. The method as claimed in claim 13, wherein said steps of analyzing comprise mirroring said first and second images and calculating a discrete Fourier transform on said mirrored images.

15. The method as claimed in claim 14, wherein said sheet material is unprinted paper.

16. The method as claimed in claim 15, wherein at least said second image is acquired using a lightbox and a CCD camera, said portion of said surface of said sheet material being approximately 6 cm by 6 cm.

17. The method as claimed in claim 12, wherein said normalized sheet material formation line output data set is limited to a predetermined range of said scale of formation.

18. The method as claimed in claim 12, wherein said normalized sheet material formation line output data set is displayed for operator consultation.

19. The method as claimed in claim 18, wherein said sheet material is unprinted paper, and said reference sheet is a reference sheet of paper having optimum production qualities.

20. The method as claimed in claim 19, wherein said intensity of local nonuniformity in said first image as a function of scale of formation is modified to be more optimum than said reference sheet, whereby said intensity of local nonuniformity in said second image is normalized with respect to a virtual reference sheet having non-real production qualities.

21. The method as claimed in claim 19, wherein steps of analyzing comprise mirroring said first and second images and calculating a discrete Fourier transform on said mirrored images.

22. The method as claimed in claim 12, wherein said sheet material is printed paper, said method determining a quality of print on said paper.

23. A method of manufacturing sheet material comprising steps of:
   acquiring an image of a portion of a surface of said sheet material at at least one transverse location on said sheet material;
   analyzing said image to determine an intensity of local nonuniformity in said image as a function of a scale of formation;
   generating an output value indicative of said sheet material quality from said intensity of local nonuniformity and said scale of formation;
   comparing said output value to an accepted value; and
   adjusting a manufacturing process parameter in response to said comparing; wherein said analyzing and said generating comprise non image-based analysis.

24. The method as claimed in claim 23, wherein said step of analyzing comprises conducting a Fourier analysis of said image.

25. The method as claimed in claim 24, wherein said step of analyzing comprises mirroring said image and calculating a discrete Fourier transform on said mirrored image.

26. The method as claimed in claim 25, wherein said sheet material is unprinted paper.

27. The method as claimed in claim 23, wherein said sheet material is unprinted paper.

* * * * *